United States Patent [19]

Inouye et al.

[11] 4,072,525
[45] Feb. 7, 1978

[54] SILVER HALIDE PHOTOGRAPHIC MATERIAL CONTAINING TWO-EQUIVALENT COLOR COUPLER

[75] Inventors: Kozo Inouye; Yukio Yokota; Kiyoshi Nakazyo, all of Minami-ashigara, Japan

[73] Assignee: Fuji Photo Film Co., Ltd., Minami-ashigara, Japan

[21] Appl. No.: 711,746

[22] Filed: Aug. 4, 1976

[30] Foreign Application Priority Data

Aug. 8, 1975 Japan .................................. 50-96435

[51] Int. Cl.$^2$ .......................... G03C 7/00; G03C 1/40
[52] U.S. Cl. .......................................... 96/55; 96/22; 96/56.1; 96/56.4; 96/56.5; 96/74; 96/100 R
[58] Field of Search ................ 96/55, 56.1, 56.4, 56.5, 96/100, 74

[56] References Cited

U.S. PATENT DOCUMENTS

| | | | |
|---|---|---|---|
| 3,770,446 | 11/1973 | Sato et al. ............................... | 96/100 |
| 3,884,700 | 5/1975 | Quaglia ................................... | 96/100 |
| 3,984,432 | 10/1976 | Piller et al. ............................ | 96/100 |

*Primary Examiner*—J. Travis Brown
*Attorney, Agent, or Firm*—Sughrue, Rothwell, Mion, Zinn and Macpeak

[57] ABSTRACT

A photographic color coupler in which a hydrogen atom at the coupling position capable of coupling with an oxidation product of an aromatic primary amine developing agent is substituted with a group represented by the following general formula:

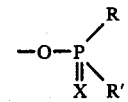

wherein R and R', which may be the same or different, each represents an alkyl group, an alkenyl group, an aryl group, an alkoxy group, an alkylthio group, an aryloxy group, a hydroxy group, or an amino group, and R and R' can combine each other to form a ring; and X represents an oxygen atom or a sulfur atom. These photographic color couplers are a novel class of two-equivalent color forming couplers which are suitable for use in color photography. A color photographic light-sensitive material containing the above described photographic color coupler and a method of forming a color image comprising developing an exposed photographic light-sensitive material in the presence of the above described photographic color coupler are also disclosed.

27 Claims, No Drawings

SILVER HALIDE PHOTOGRAPHIC MATERIAL CONTAINING TWO-EQUIVALENT COLOR COUPLER

BACKGROUND OF THE INVENTION

1. Field of the Invention

The present invention relates to a photographic color coupler, more particularly, it relates to a novel class of two-equivalent color couplers, a color photographic light-sensitive material containing such color couplers and a method of forming images using such color couplers.

2. Description of the Prior Art

It is well known that an oxidized aromatic primary amine developing agent reacts with a dye forming coupler to form a color image by color development after exposure of a silver halide photographic light-sensitive material to light. In this method, a color reproduction process according to a conventional subtractive method is applied to form a cyan, magenta or yellow color image which is in a complementary relationship with red, green or blue color. For instance, a phenol derivative or a naphthol derivative is used as a coupler for forming a cyan color image, a 5-pyrazolone derivative, a pyrazolobenzimidazole derivative or a indazolone derivative is used for forming a magenta color image, and a pivaloylacetanilide derivative or a benzoylacetanilide derivative is used for forming a yellow color image.

In a color photographic process, a color forming coupler which is added to a developer solution or incorporated in a light-sensitive photographic emulsion layer or other color image forming layer reacts with an oxidation product of a color developing agent formed upon development to form a non-diffusible color image. Almost all conventional couplers are four-equivalent couplers, that is, theoretically, they stoichiometrically require four mols of exposed silver halide as an oxidizing agent for the formation of one mole of a dye. Incorporation of a large amount of silver halide in a light-sensitive layer is disadvantageous because the sharpness of the images formed deteriorates due to increased light scattering in the emulsion layer or because the rate of processing the light-sensitive material is reduced due to increased thickness of the emulsion layer. Further, the formation of dyes by these four-equivalent couplers has the disadvantage that a strong oxidizing agent must be employed in a subsequent processing step, because the complete formation of the dyes does not occur in a color development bath.

In order to overcome these disadvantages of two-equivalent couplers, that is, couplers which require only two mols of exposed silver halide for forming one mol of a dye, has been proposed.

Two-equivalent couplers have a structure in which one hydrogen atom of the coupling position, such as the para-position of a phenolic hydroxy group, an active methylene group at the 4-position of a 5-pyrazolone or an active methylene group of an acylacetanilide, is substituted with a releasable group. Examples of releasable groups are a sulfonamido group as described in U.S. Pat. No. 3,737,316, an imido group as described in U.S. Pat. No. 3,749,735, a sulfonyl group as described in U.S. Pat. No. 3,622,328, an aryloxy group as described in U.S. Pat. No. 3,476,563, an aryloxy group as described in U.S. Pat. No. 3,419,391, a thiocyano group as described in U.S. Pat. Nos. 3,214,377 and 3,253,924, a carbamoyl group as described in Japanese Pat. application (OPI) 74539/1974, an imido group as described in Japanese Pat. application (OPI) 53436/1974, an aminosulfonyloxy group as described in Japanese Patent Publication 12661/1974 and a sulfinyloxy group as described in Japanese Pat. Publication 12660/1974.

However, these known couplers are not always satisfactory because they have the disadvantages that coupling reactivity is insufficient, dispersibility is inferior, resulting in difficulties in coating, remarkably high color fog is produced, the synthesis of the couplers is very difficult, the storability of the color images formed is poor, and the like.

SUMMARY OF THE INVENTION

One object of the present invention is to provide a novel class of two-equivalent couplers having good dispersibility and which do not give rise to difficulties on coating and which are suitable for producing light-sensitive materials for a color photographic process according to a subtractive method.

Another object of the present invention is to provide a method of forming a cyan, magenta or yellow dye image which comprises developing a silver halide emulsion in the presence of a novel two-equivalent coupler.

Still another object of the present invention is to provide a color photographic light-sensitive material having a silver halide emulsion layer containing a novel coupler.

Yet another object of the present invention is to provide a means for improving the sharpness of the image formed by decreasing the amount of silver halide present in a photographic emulsion by using a novel coupler.

A further object of the present invention is to provide a two-equivalent coupler which forms a color image having a good spectral absorption characteristic and good stability to heat and high humidity on exposure for a long period of time.

A still further object of the present invention is to provide a novel coupler which forms a color image with high sensitivity, high gamma and high density by color development.

A still further object of the present invention is to provide a color developer solution containing a novel two-equivalent coupler.

The inventors have found that the above described objects can be achieved by a photographic two-equivalent coupler in which a hydrogen atom at the coupling position capable of coupling with an oxidation product of an aromatic primary amine developing agent is substituted with a group represented by the following general formula:

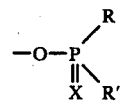

The group represented by the general formula is a group capable of releasing upon coupling of the coupler with an oxidation product of an aromatic primary amine developing agent to form a dye. In the formula, R and R' each represents an alkyl group, an alkenyl group, an aryl group, an alkoxy group, an alkylthio group, an aryloxy group, a hydroxy group, or an amino group and R and R' can form a ring structure (for example, a 5-membered or 6-membered ring), R and R' can be the same or different; and X represents an oxygen atom or sulfur atom.

DETAILED DESCRIPTION OF THE INVENTION

The coupler of the present invention provides high sensitivity, high gamma and high maximum density, and, further, can provide sufficient maximum density even in a short processing time, and, thus, the coupler is suitable for use not only in a conventional processing system but also a rapid processing system.

The coupler of the present invention is particularly excellent in view of the heat and moisture resistance of dye images formed.

The coupler according to the present invention includes a phenol or naphthol type cyan color forming coupler in which a hydrogen atom of the coupling position, that is, the para-position to the phenolic hydroxy group, is substituted with a group of the formula

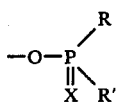

which can be released upon coupling with an oxidized aromatic primary amine developing agent.

Further, the couplers according to the present invention include a 5-pyrazolone type or a pyrazolobenzimidazole type magenta color forming coupler in which a hydrogen atom of the active methylene group is substituted with a group of the formula

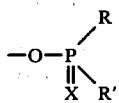

Moreover, the couplers according to the present invention include an open-chain ketomethylene type yellow color forming coupler, for example, a pivaloylacetanilide, a benzoylacetanilide, a malondiamide, a cyanoacetanilide, a benzothiadiazine as described in U.S. Pat. Nos. 3,841,880 and 3,874,948, a benzothiazolyl acetamide, a benzothiazolyl acetate, a benzoxazolyl acetamide, a benzoxazolyl acetate, a benzimidazolyl acetamide or a benzimidazolyl acetate in which a hydrogen atom of the active methylene group is substituted with a group of the formula

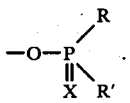

Preferred couplers according to the present invention can be represented by the following general formula (I):

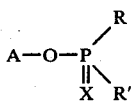

wherein A represents an image forming coupler residue containing a naphthol nucleus, a phenol nucleus, a 5-pyrazolone nucleus, a pyrazolobenzimidazole nucleus, a pivaloylacetanilide nucleus, a benzoylacetanilide nucleus, a malondiamide nucleus, a cyanoacetanilide nucleus, a benzothiadiazine nucleus as described in U.S. Pat. No. 3,841,880, a benzothiazolylacetamide nucleus, a benzothiazolylacetate nucleus, a benzoxazolylacetamide nucleus, a benzoxazolylacetate nucleus, a benzimidazolylacetamide nucleus, or a benzimidazolylacetate nucleus; wherein the group of the formula

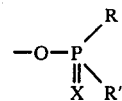

is a group which is bonded to the coupling position of the above described coupler residue and is released upon coupling with an oxidized aromatic primary amine developing agent to form a dye; and R, R' and X each has the same meaning as defined in the above described general formula.

The alkyl group represented by R and R' includes a straight, branched or cyclic alkyl group having 1 to 32 carbon atoms, preferably 1 to 20 carbon atoms (for example, methyl, ethyl, propyl, octyl, octadecyl, isopropyl, cyclohexyl, etc.). The alkenyl group represented by R and R' includes a straight or branched chain alkenyl group having 1 to 32 carbon atoms, preferably 1 to 20 carbon atoms (for example, 2-pentenyl, etc.). The aryl group represented by R and R' includes a phenyl group, a naphthyl group, etc. The alkoxy group and alkylthio group represented by R and R' each includes a straight, branched or cyclic alkoxy group or alkylthio group having 1 to 32 carbon atoms, preferably, 1 to 20 carbon atoms (for example, methoxy, ethoxy, octadecyloxy, sec-butyloxy, cyclohexyloxy, ethylthio, butylthio, octadecylthio, etc.). The aryloxy group represented by R and R' includes a phenoxy group, a naphthoxy group, etc. The amino group represented by R and R' includes an alkylamino group (where preferred alkyl moieties have from 1 to 20 carbon atoms, for example, dimethylamino, butylamino, etc.), an arylamino group (for example, anilino, etc.), and the like. Unless otherwise indicated, any aryl moiety represented by R and R' or aryl moiety which forms a part of another moiety represented by R and R' is preferably a mono or di-cyclic aryl moiety.

The above described alkyl group, alkenyl group, aryl group, alkoxy group, alkythio group, aryloxy group and amino group can be substituted with a halogen atom (for example, chlorine, bromine, etc.), a nitro group, a cyano group, a hydroxy group, an alkyl group (for example, an alkyl group having 1 to 20 carbon atoms such as methyl, ethyl, etc.), a carboxy group, a sulfo group, an amino group (for example, amino, alkylamino (for example, alkylamino having 1 to 20 carbon atoms such as methylamino, ethylamino, etc.), dialkylamino (where any alkyl moiety preferably has 1 to 20 carbon atoms, for example, dimethylamino, diethylamino, etc.), anilino, N-alkylanilino (where the alkyl moiety preferably has 1 to 20 carbon atoms, for example, N-methylanilino, etc.), and the like), an aryl group (where the aryl moiety is preferably mono or di-cyclic, for example, phenyl, naphthyl, etc.), an alkoxycarbonyl group (where the alkoxy moiety preferably has 1 to 20 carbon atoms, for example, methoxycarbonyl, ethoxycarbonyl, etc.), an aryloxycarbonyl group (where the aryl moiety is preferably mono or di-cyclic for example, phenoxycarbonyl, etc.), an acyloxy group (where the acyl moiety preferably has 2 to 20 carbon atoms, for example, acetyloxy, benzoyloxy, etc.), an amido group (most preferably having up to 20 carbon atoms, for example, acetamide, methanesulfonamido, sulfonamido, etc.), an imido group (preferably having a total of 2 to 20 carbon atoms, for example, succinimido, etc.), a carbamoyl group (preferably having a total of 1 to 20 carbon atoms, for example, N,N-diethylcarbamoyl, etc.), a sulfamoyl group (most preferably having up to 20 carbon atoms, for example, N,N-diethylsulfamoyl, etc.), a ureido group (preferably having a total of 1 to 20 carbon atoms, for example, 3-phenylureido, etc.), an alkoxy group (for example, an alkoxy group having 1 to 20 carbon atoms such as ethoxy, octadecyloxy, etc.), an aryloxy group (where the aryl moiety is preferably mono or di-cyclic, for example, phenoxy, p-tert-butylphenoxy, 4-hydroxy-3-tert-butylphenoxy, etc.), an alkylthio group (for example, an alkylthio group having 1 to 20 carbon atoms such as ethylthio, etc.), an arylthio group (where the aryl moiety is preferably mono or di-cyclic, for example, phenylthio, etc.), a heterocyclic group (most preferably comprising a 5- or 6-membered ring containing at least one of N, O or S, for example, 2-thiazolyl, 2-benzothiazolyl, 2-benzoxazolyl, pyridyl, etc.), a heterocyclic thio group (most preferably comprising a 5- or 6-membered ring containing at least one of N, O or S, for example, 1-phenyl-5-tetrazolylthio, etc.), an arylazo group (where the aryl moiety is preferably mono or di-cyclic, for example, 4-chlorophenylazo, 4-methoxyphenylazo, α-naphthylazo, etc.), a group containing a chromophore, or other conventional substituents.

The group containing a chromophore described above is a group which renders the coupler colored, and includes, for example, an azo dye residue such as those represented by the following formulae:

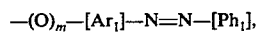

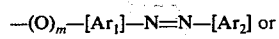

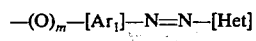

wherein $m$ is 0 or 1; —[Ar$_1$]— represents an arylene group (for example, a phenylene group, a naphthylene group, etc.); —[Ph$_1$] represents a phenyl group having a water soluble group or a hydrophilic group (as the water soluble group, for example, —SO$_3$M, —COOM, etc., wherein M represents a cation such as an alkali metal ion, an ammonium ion, etc., or a hydrogen atom, and as the hydrophilic group, for example, an amido group, etc.); —[Ar$_2$] represents a hydroxynaphthyl group having a water soluble group or a hydrophilic group (as the water soluble group, for example —SO$_3$M, —COOM, etc., wherein M represents a cation such as an alkali metal ion, an ammonium ion, etc., or a hydrogen atom, and as the hydrophilic group, for example, an amido group, etc.), and includes, for example, the following:

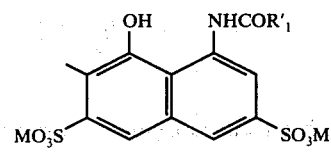

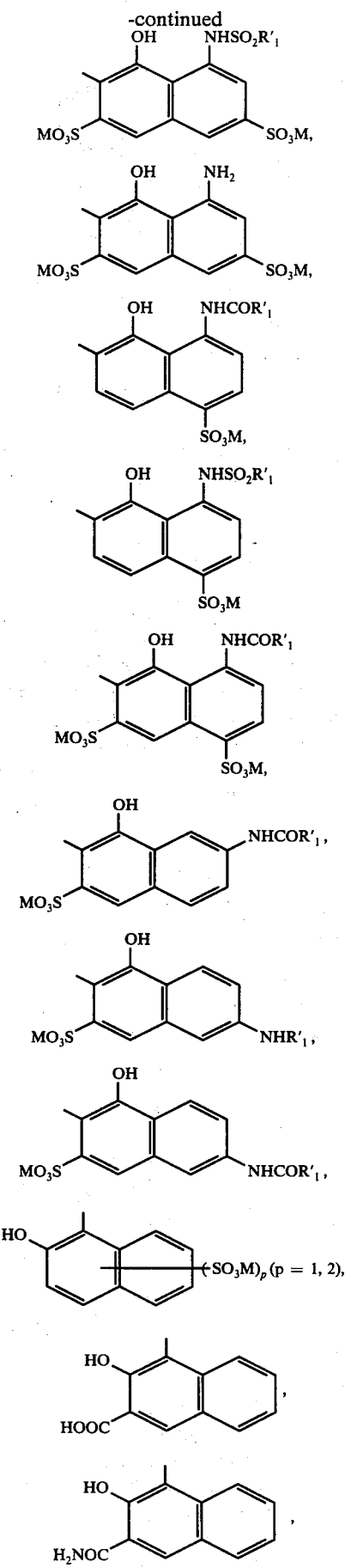

-continued

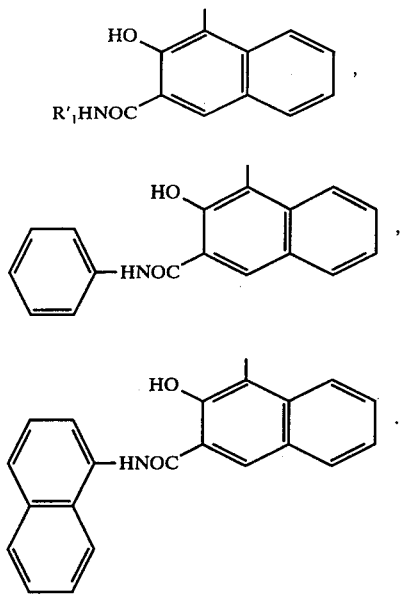

—[Het] represents an aromatic heterocyclic group, preferably an aromatic heterocyclic group having a water soluble group such as —SO₃M or —COOM, wherein M represents a cation such as an alkali metal ion, an ammonium ion, etc., or a hydrogen atom, even more preferably a 5- or 6-membered nitrogen containing aromatic heterocyclic group, and includes, for example, the following:

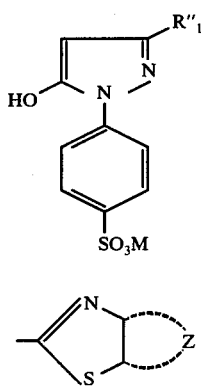

wherein Z represents the non-metallic atomic group necessary to form a fused aromatic ring, e.g., benzene or naphthalene; M represents a cation such as an alkali metal ion, an ammonium ion, etc., or a hydrogen atom; R'₁ represents an alkyl group having 1 to 7 carbon atoms, a hydrogen atom, a phenyl group, or a naphthyl group; and R''₁ represents an amino group, an alkyl group having 1 to 5 carbon atoms, an acylamino group, most preferably where the acyl moiety contains 1 to 10 carbon atoms, a sulfonamido group, a ureido group, an alkoxycarbonyl group, most preferably where the alkoxy moiety contains from 2 to 10 carbon atoms, a substituted group thereof (which applies to all of the above groups), or a carboxy group; an azomethine dye residue such as those represented by the following formulae:

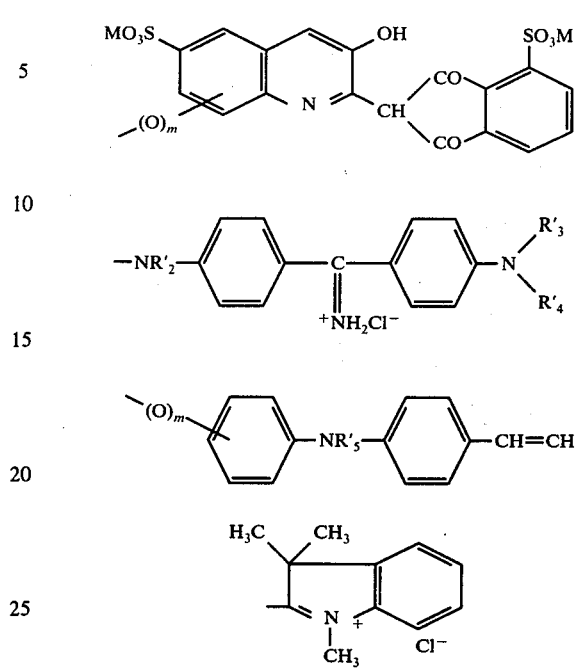

wherein $m$ is 0 or 1; M represents a cation such as an alkali metal cation, an ammonium ion, etc., or a hydrogen atom; and R'₂, R'₃, R'₄ and R'₅ each represents an aliphatic hydrocarbon group, for example, an alkyl group having 1 to 5 carbon atoms; a xanthene type dye residue such as those represented by the following formula:

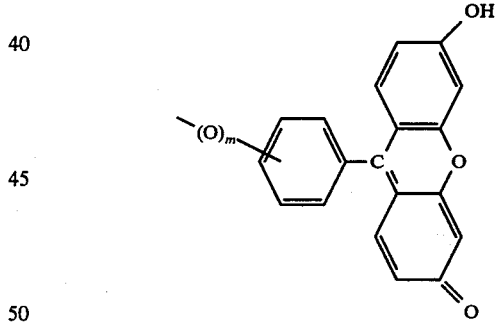

wherein $m$ is 0 or 1; an azine type dye residue such as those represented by the following formula:

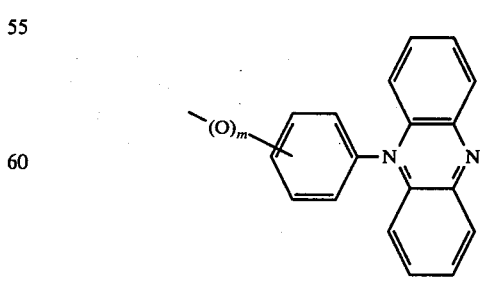

wherein $m$ is 0 or 1; an indoaniline type dye residue such as those represented by the following formulae:

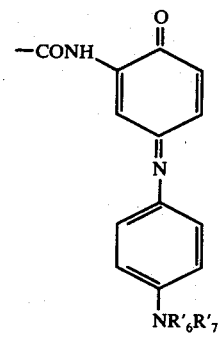

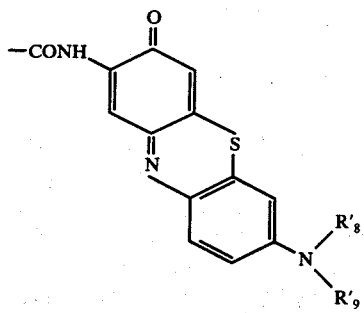

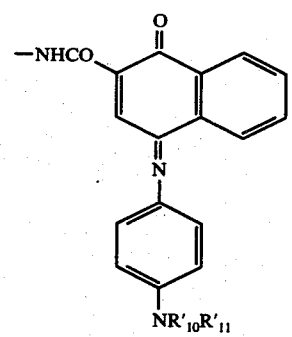

wherein $R'_6$, $R'_7$, $R'_8$, $R'_9$, $R'_{10}$, and $R'_{11}$ each represents an aliphatic hydrocarbon group, for example, an alkyl group having 1 to 5 carbon atoms;

an indophenol type dye residue such as those represented by the following formula:

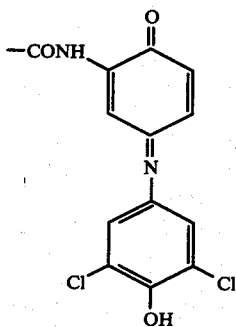

or an onium salt thereof, etc.;

an anthraquinone type dye residue such as those represented by the following formulae:

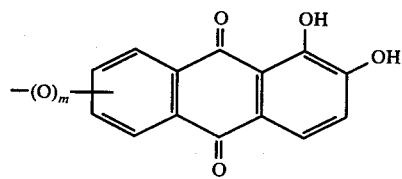

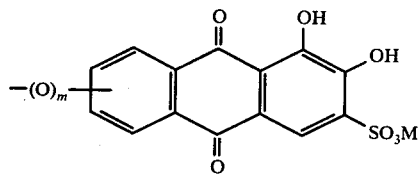

wherein $m$ is 0 or 1 and M is as earlier defined; and other known groups containing a dye residue.

Of the couplers according to the present invention, particularly preferred couplers are represented by the following general formula (II):

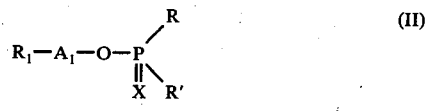

wherein $A_1$ represents a cyan image forming coupler residue containing a phenol nucleus, a cyan image forming coupler residue containing an α-naphthol residue, a 5-pyrazolone type or pyrazolobenzimidazole type magenta image forming coupler residue, or a pivaloylacetanilide type, benzoylacetanilide type, malondiamide type, cyanoacetanilide type, benzothiadiazine type as described in U.S. Pat. No. 3,841,880, benzothiazolyl acetamide type, benzothiazolyl acetate type, benzoxazolyl acetamide type, benzoxazolyl acetate type, benzimidazolyl acetamide type or benzimidazolyl acetate type yellow image forming coupler residue;

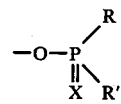

is a group which is bonded to the coupling position of the above mentioned coupler residue and is released upon coupling with an oxidized aromatic primary amine developing agent to form a dye; R, R' and X each has the same meaning as R, R' and X in general formula (I); and $R_1$ represents a hydrogen atom, a halogen atom such as chlorine, bromine, etc., a nitro group, a cyano group, a hydroxy group, a sulfo group, a carboxy group, an alkyl group having 30 or less carbon atoms, and particularly, an alkyl group having 1 to 20 carbon atoms such as methyl, isopropyl, pentadecyl, eicosyl, etc., an alkoxy group having 30 or less carbon atoms, and particularly, an alkoxy group having 1 to 20 carbon atoms such as methoxy, isopropoxy, pentadecyloxy, eicosyloxy, etc., an aryloxy group, most preferably where the aryl moiety is mono or di-cyclic, such as phenoxy, p-tert-butylphenoxy, etc., an acylamino group represented by the following formulae (III) to (VI), a carbamoyl group represented by the following formulae (VII) and (VIII), an oxycarbonyl group represented by the following formula (IX), or a sulfamoyl group represented by the following formulae (X) and (XI).

$$-NH-CO-Z \quad (III)$$
$$-NH-SO_2-Z \quad (IV)$$

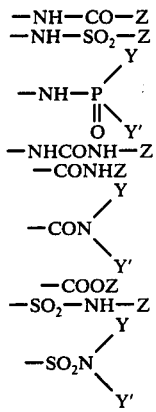
(V)

$$-NHCONH-Z \quad (VI)$$
$$-CONHZ \quad (VII)$$

(VIII)

$$-COOZ \quad (IX)$$
$$-SO_2-NH-Z \quad (X)$$

(XI)

wherein Z represents a straight or branched chain alkyl group having 1 to 32 carbon atoms, preferably 1 to 20 carbon atoms (for example, methyl, ethyl, isopropyl, etc.), a cycloalkyl group (for example, cyclopropyl, cyclohexyl, norbornyl, etc.), or an aryl group (most preferably where the aryl group is mono or di-cyclic, for example phenyl, naphthyl, etc.); wherein the above described alkyl group and aryl group can be substituted with a halogen atom (for example, chlorine, bromine, etc.), a nitro group, a cyano group, a hydroxy group, an alkyl group (for example, alkyl having 1 to 20 carbon atoms such as methyl, ethyl, etc.), a carboxy group, an amino group (for example, amino, alkylamino (for example, alkylamino having 1 to 20 carbon atoms such as methylamino, ethylamino, etc.), dialkylamino (for example, dimethylamino, diethylamino, etc.), anilino, N-alkylanilino (most preferably where any alkyl moiety has 1 to 20 carbon atoms, for example, N-methylanilino, etc.), and the like, an aryl group (most preferably a mono or di-cyclic aryl group, for example, phenyl, naphthyl, etc.), an alkoxycarbonyl group (where the alkoxy moiety most preferably has 1 to 20 carbon atoms, for example, methoxycarbonyl, ethoxycarbonyl, etc.), an acyloxycarbonyl group, most preferably where the acyl moiety has 2 to 20 carbon atoms, an amido group (most preferably having up to 20 carbon atoms, for example, acetamido, methanesulfonamido, etc.), an imido group (most preferably having 2 to 20 carbon atoms, for example, succinimido, etc.), a carbamoyl group (most preferably having 1 to 20 carbon atoms, for example, hexadecylcarbamoyl, N,N-dihexylcarbamoyl, etc.), a sulfamoyl group (most preferably having up to 20 carbon atoms, for example, ethylsulfamoyl, N,N-diethylsulfamoyl, etc.), an alkoxy group (for example, alkoxy having 1 to 20 carbon atoms such as ethoxy, octadecyloxy, etc.), an aryloxy group (where the aryl moiety is most preferably mono or di-cyclic, for example, phenoxy, p-tert-butylphenoxy, 4-hydroxy-3-tert-butylphenoxy, etc.), and the like; Y and Y' each represents the above described or —OZ, —NH-Z or

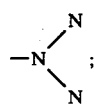

and $R_1$ can contain conventional substituents in addition to the above described substituents.

Of the compounds represented by the above described general formula (II), particularly preferred compounds are represented by general formulae (XII), (XIII), (XIV), (XV), (XVI) and (XVII):

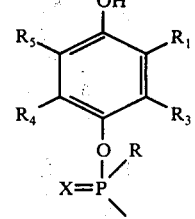
(XII)

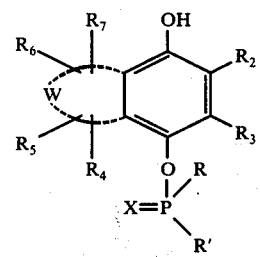
(XIII)

wherein R, R', $R_1$ and X each has the same meaning as R, R', $R_1$ and X of general formula (II); $R_2$ represents a hydrogen atom, an alkyl group having 30 or less carbon atoms, and, particularly, an alkyl group having 1 to 20 carbon atoms (for example, methyl, isopropyl, pentadecyl, etc.) or a carbamoyl group represented by general formulae (VII) and (VIII) as described for $R_1$ in general formula (II); $R_3$, $R_4$, $R_5$, $R_6$ and $R_7$ each represents a hydrogen atom, a halogen atom, an alkyl group, an aryl group, an alkoxy group, an alkylthio group, a heterocyclic group, most preferably comprising a 5- or 6-membered ring containing at least one of N, O or S, an amino group, a carbonamido group, a sulfonamido group, a sulfamoyl group or a carbamoyl group; and W represents the non-metallic atomic group necessary to form a 5-membered or 6-membered ring such as a benzene ring, a cyclohexene ring, a cyclopentene ring, a thiazole ring, an oxazole ring, an imidazole ring, a pyridine ring, a pyrrole ring, a tetrahydropyridine ring, and the like.

Examples of the groups for $R_3$ are a hydrogen atom, a halogen atom (for example, chlorine, bromine, etc.), a primary, secondary or tertiary alkyl group having 1 to 20 carbon atoms (for example, methyl, propyl, isopropyl, n-butyl, sec-butyl, tert-butyl, hexyl, dodecyl, 2-chlorobutyl, 2-hydroxyethyl, 2-phenylethyl, 2-(2,4,6-trichlorophenyl)ethyl, 2-aminoethyl, etc.), an alkoxy group or an alkylthio group having 1 to 20 carbon atoms (for example, methoxy, octadecyloxy, ethylthio, etc.), an aryl group (for example, phenyl, 4-methylphenyl, 2,4,6-trichlorophenyl, 3,5-dibromophenyl, 4-trifluoromethylphenyl, 2-trifluoromethylphenyl, 3-trifluoromethylphenyl, naphthyl, 2-chloronaphthyl, 3-ethylnaphthyl, etc.) and a heterocyclic group (for example, a benzofuranyl group, a furyl group, a thiazolyl group, a benzothiazolyl group, a naphthothiazolyl group, an oxazolyl group, a benzoxazolyl group, a naphthoxazolyl group, a pyridyl group, a quinolyl group, etc.). Further examples of $R_3$ are an amino group (for example, amino, methylamino, diethylamino, dodecylamino, phenylamino, tolylamino, 4-(3-sulfobenzamido)-anilino, 4-cyanophenylamino, 2-trifluoromethylphenylamino, benzothiazolylamino, etc.), a carbonamido group (for example, an alkyl carbonamido group, where the alkyl moiety preferably has 1 to 20 carbon atoms, such as ethylcarbonamido, decylcarbonamido, phenylethylcarbonamido, etc., an arylcarbonamido group, where the aryl moiety is preferably mono or di-cyclic aryl, such as phenylcarbonamido, 2,4,6-trichlorophenylcarbonamido, 4-methylphenylcarbonamido, 2-ethoxyphenylcarbonamido, 3-[α-(2,4-di-tert-amylphenoxy)acetamido]benzamido, naphthylcarbonamido, etc., a heterocyclic carbonamido group, where preferred heterocyclic moieties include at least one N, O or S atom, such as thiazolylcarbonamido, benzothiazolylcarbonamido, naphthothiazolylcarbonamido, oxazolylcarbonamido, benzoxazolylcarbonamido, imidazolylcarbonamido, benzimidazolylcarbonamido, etc.), a sulfonamido group (for example, an alkylsulfonamido group, where the alkyl moiety preferably has 1 to 20 carbon atoms, such as butylsulfonamido, dodecylsulfonamido, phenylethylsulfonamido, etc., an arylsulfonamido group, where the aryl moiety is preferably mono or di-cyclic aryl, such as phenylsulfonamido, 2,4,6-trichlorophenylsulfonamido, 2-methoxyphenylsulfonamido, 3-carboxyphenylsulfonamido, naphthylsulfonamido, etc., a heterocyclic sulfonamido group, where preferred heterocyclic moieties include at least one N, O or S atom, such as thiazolylsulfonamido, benzothiazolylsulfonamido, imidazolylsulfonamido, benzimidazolylsulfonamido, pyridylsulfonamido, etc.), a sulfamoyl group (preferably having up to 20 carbon atoms, for example, an alkylsulfamoyl group such as propylsulfamoyl, acetylsulfamoyl, pentadecylsulfamoyl, octadecylsulfamoyl, etc., an arylsulfamoyl group, where the aryl moiety is preferably mono or di-cyclic aryl, such as phenylsulfamoyl, 2,4,6-trichlorophenylsulfamoyl, 2-methoxyphenylsulfamoyl, naphthylsulfamoyl, etc., a heterocyclic sulfamoyl group, where preferred heterocyclic moieties include at least one N, O or S atom, such as thiazolylsulfamoyl, benzothiazolylsulfamoyl, oxazolylsulfamoyl, benzimidazolylsulfamoyl, pyridylsulfamoyl, etc.), and a carbamoyl group (for example, an alkylcarbamoyl group, where the alkyl moiety most preferably has 1 to 20 carbon atoms, such as ethylcarbamoyl, octylcarbamoyl, pentadecylcarbamoyl, octadecylcarbamoyl, etc., an arylcarbamoyl group, preferably where the aryl moiety is mono or di-cyclic aryl, such as phenylcarbamoyl, 2,4,6-trichlorophenylcarbamoyl, etc., a heterocyclic carbamoyl group, where preferred heterocyclic moieties include at least one N, O or S atom, such as thiazolylcarbamoyl, benzothiazolylcarbamoyl, oxazolylcarbamoyl, imidazolylcarbamoyl, benzimidazolylcarbamoyl, etc.). Examples of $R_4$, $R_5$, $R_6$ and $R_7$ are as defined for $R_3$. Examples of W, the non-metallic atomic group necessary to form a fused 5-membered or 6-membered ring, include a benzene ring, a cyclohexene ring, a cyclopentene ring, a thiazole ring, an oxazole ring, an imidazole ring, a pyridine ring, a pyrrole ring, a tetrahydropyridine ring, and the like.

Magenta Couplers

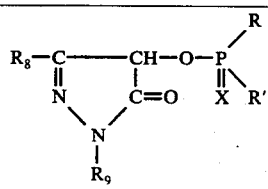

(XIV)

-continued
Magenta Couplers (XV)

wherein R, R' and X each has the same meaning as R, R' and X of general formula (II); $R_8$ and $R_{10}$ each represents an alkyl group (for example, alkyl having 1 to 20 carbon atoms such as methyl, octadecyl, etc.), an alkoxy group (for example, alkoxy having 1 to 20 carbon atoms such as methoxy, ethoxy, etc.), a ureido group (for example, phenylureido, etc.), or a substituted amino group (for example, alkylamino, where the alkyl moiety preferably has 1 to 20 carbon atoms, such as methylamino, ethylamino, etc., dialkylamino, where the alkyl moiety preferably has 1 to 20 carbon atoms, such as diethylamino, dibutylamino, etc., cycloalkylamino, where the alkyl moiety preferably has 1 to 20 carbon atoms, such as pyrrolidino, morpholino, etc., arylamino, where the aryl moiety is preferably mono or di-cyclic aryl, such as anilino, 2-chloro-5-tetradecanamidoanilino, etc., acylamino, where the acyl moiety preferably has 2 to 20 carbon atoms, such as acetamido, benzamido, etc., N-alkylacylamino, where preferred alkyl moieties have 1 to 20 carbon atoms and preferred acyl moieties have 2 to 20 carbon atoms, such as N-methylbenzamido, etc.), $R_9$ represents an alkyl group (for example, alkyl having 1 to 20 carbon atoms such as methyl, ethyl, etc.), an aralkyl group (where preferred alkyl moieties have 1 to 20 carbon atoms and preferred aryl moieties are mono or di-cyclic aryl, for example, benzyl, etc.), an aryl group, preferably a mono or di-cyclic aryl group, or a heterocyclic group (where preferred heterocyclic moieties include at least one N, O or S atom, for example, 2-pyridyl, 2-benzothiazolyl, etc.). Examples of aryl groups for $R_9$ include a phenyl group, a naphthyl group, etc., and these aryl groups can be substituted, if desired. Examples of the substituents are a halogen atom (for example, chlorine, bromine, etc.), an alkyl group (for example, alkyl having 1 to 20 carbon atoms such as methyl, ethyl, etc.), an aryl group (where the aryl moiety preferably is mono or di-cyclic aryl, for example, phenyl, naphthyl, etc.), an alkoxy group (for example, alkoxy having 1 to 20 carbon atoms such as methoxy, ethoxy, etc.), an aryloxy group (where the aryl moiety preferably is mono or di-cyclic aryl, for example, phenoxy, etc.), an alkoxycarbonyl group (for example, alkoxycarbonyl having 1 to 20 carbon atoms such as methoxycarbonyl, tetradecyloxycarbonyl, etc.), an aryloxycarbonyl group (where the aryl moiety preferably is mono or di-cyclic aryl, for example, phenoxycarbonyl, etc.), an alkoxysulfonyl group (for example, alkoxysulfonyl having 1 to 20 carbon atoms such as methoxysulfonyl, etc.), an acylamino group (where the acyl moiety preferably has 2 to 20 carbon atoms, for example, acetamido, tetradecanamido, benzamido, etc.), a carbamoyl group (preferably having 1 to 20 carbon atoms, for example, ethylcarbamoyl, etc.), a sulfamoyl group (preferably having up to 20 carbon atoms, for example, ethylsulfamoyl, etc.), and the like. Q represents the atomic group necessary to form a heterocyclic ring, most preferably comprising a 5- or 6-membered ring containing at least one of N, O or S.

Yellow Couplers

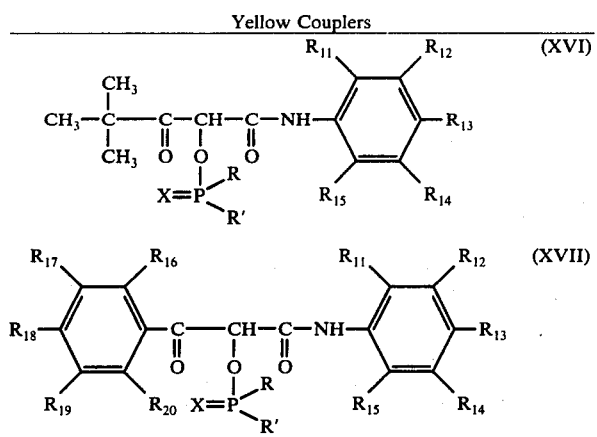

wherein R, R' and X each has the same meaning as R, R' and X of general formula (II); $R_{11}$ represents a hydrogen atom, a halogen atom such as chlorine, bromine, etc., a nitro group, a cyano group, a hydroxy group, a sulfo group, a carboxy group, an alkyl group having 1 to 20 carbon atoms such as ethyl, eicosyl, etc., an alkoxy group having 1 to 20 carbon atoms such as methoxy, octadecyloxy, etc., an aryloxy group, where the aryl moiety is preferably mono or dicyclic aryl, such as phenoxy, p-tert-butylphenoxy, etc., an acylamino group represented by general formulae (III) to (VI), a carbamoyl group represented by general formulae (VII) and (VIII), an oxycarbonyl group represented by general formula (IX) or a sulfamoyl group represented by general formulae (X) and (XI) as described for $R_1$ in general formula (II); and $R_{12}$, $R_{13}$, $R_{14}$, $R_{15}$, $R_{16}$, $R_{17}$, $R_{18}$, $R_{19}$ and $R_{20}$ each represents a group as defined for $R_{11}$.

Typical examples of couplers which can be used in the present invention are described in the following, however, the couplers are not to be construed as being limited to these examples.

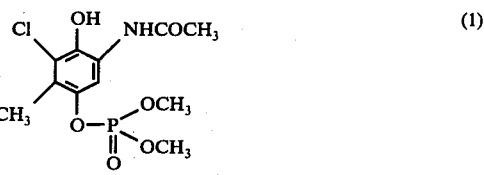

(1)

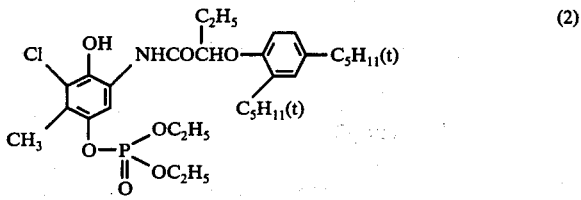

(2)

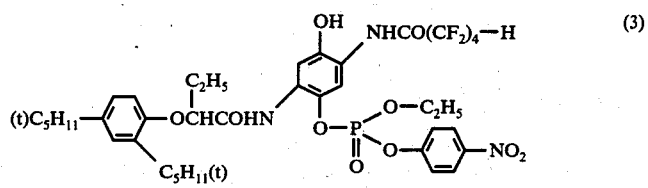

(3)

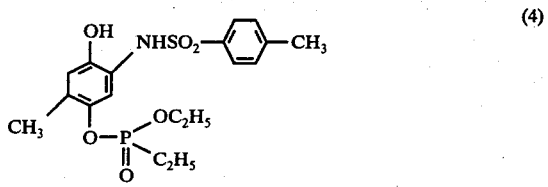

(4)

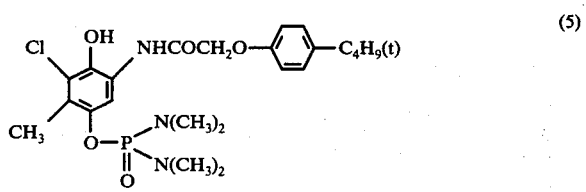

(5)

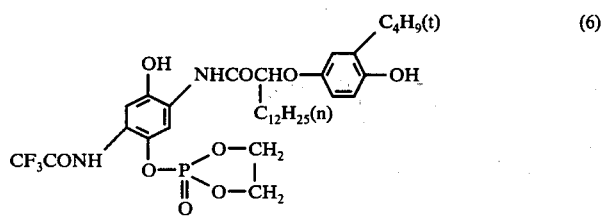

(6)

-continued
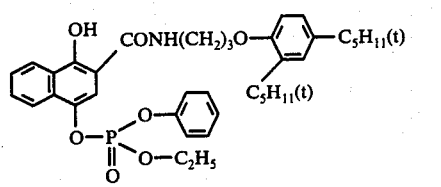
(7)
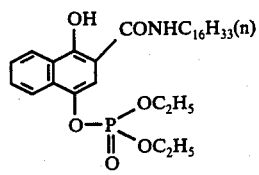
(8)
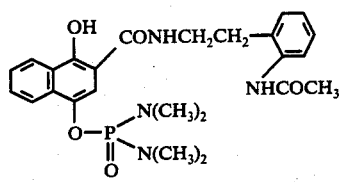
(9)
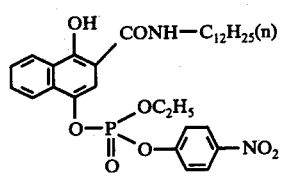
(10)
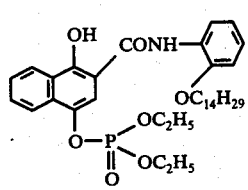
(11)
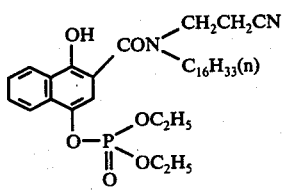
(12)
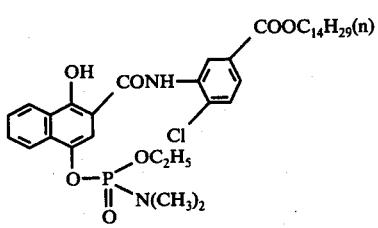
(13)
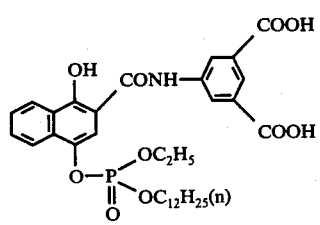
(14)
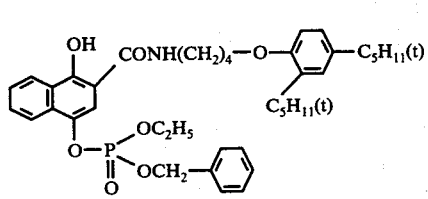
(15)

-continued
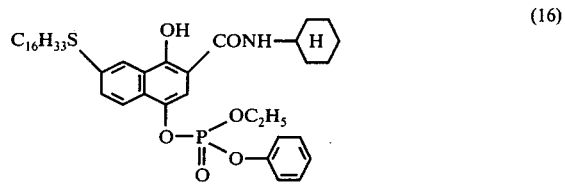
(16)
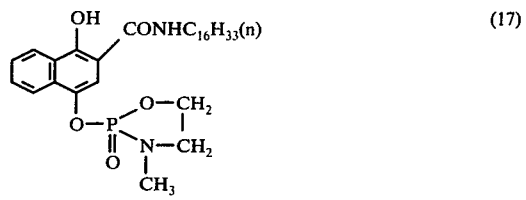
(17)
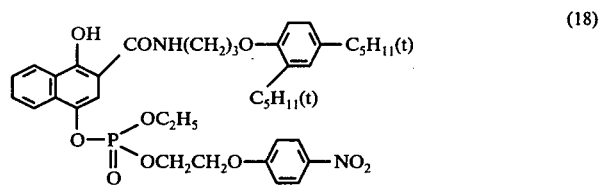
(18)
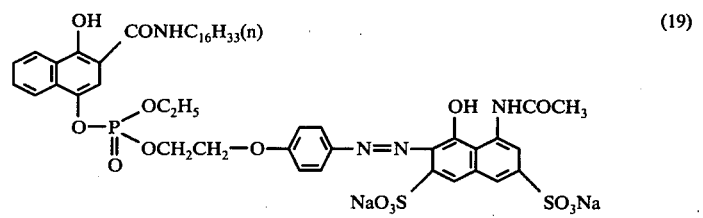
(19)
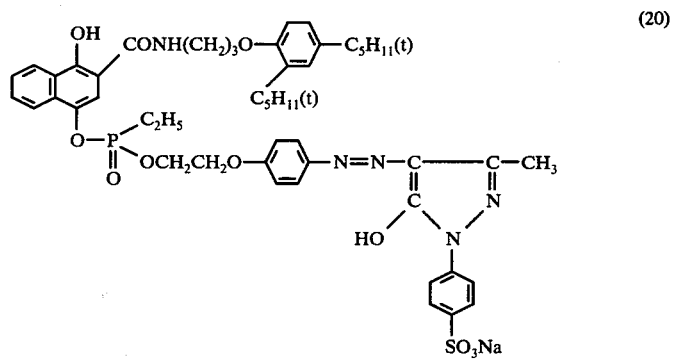
(20)
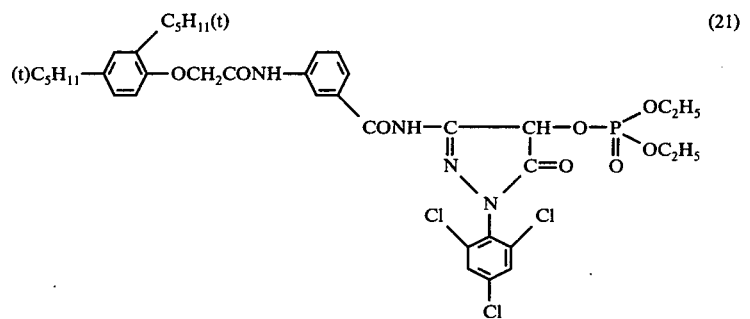
(21)

-continued
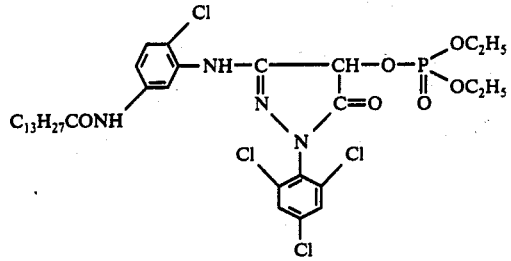 (22)
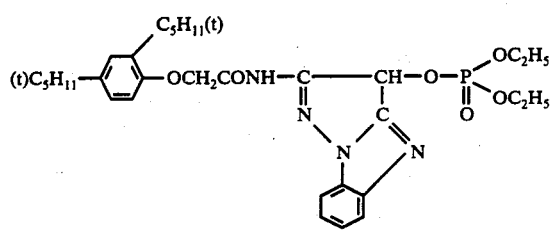 (23)
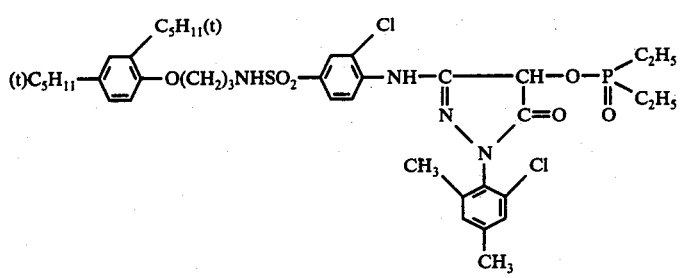 (24)
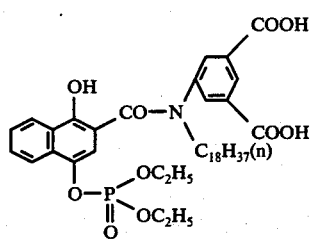 (25)
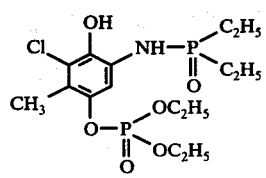 (26)
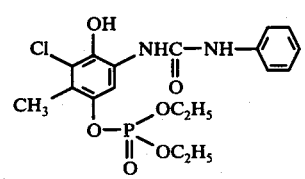 (27)
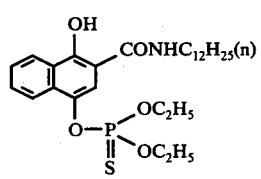 (28)

-continued
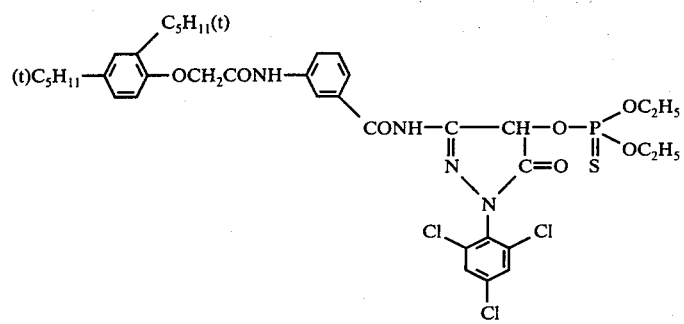  (29)
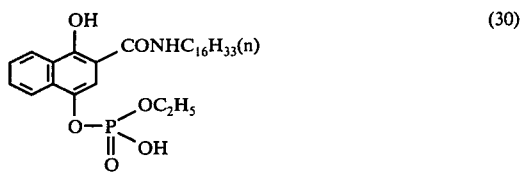  (30)
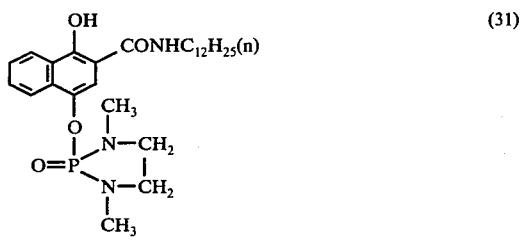  (31)
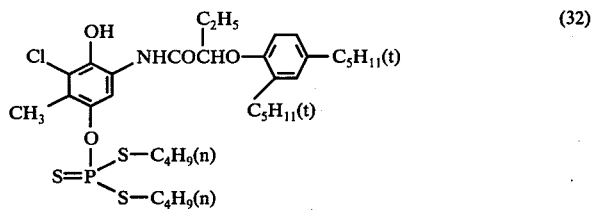  (32)
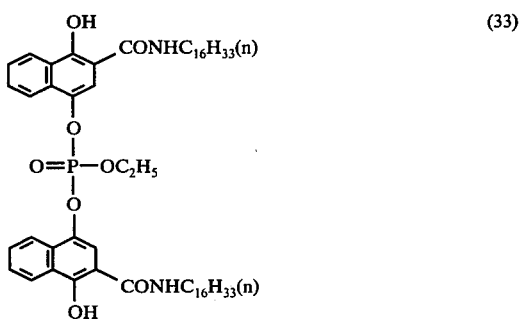  (33)
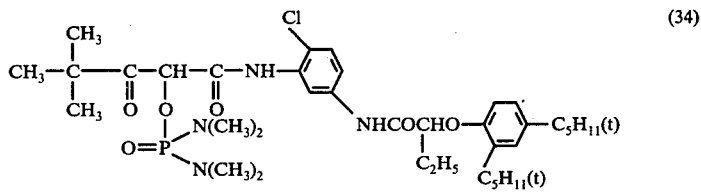  (34)
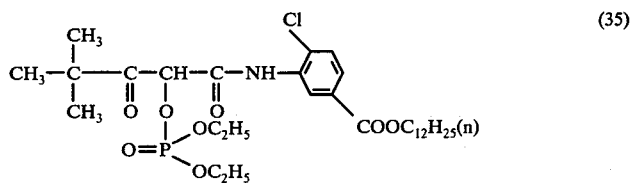  (35)

-continued

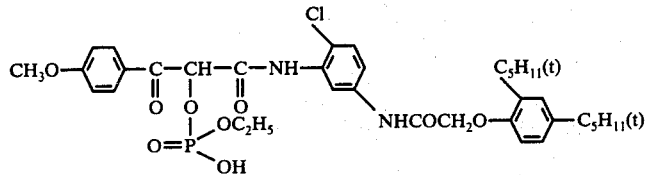
(36)

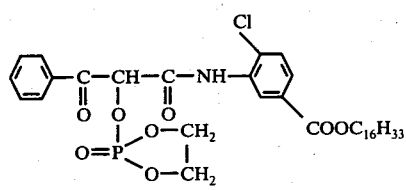
(37)

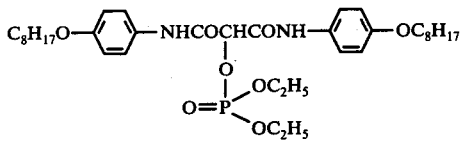
(38)

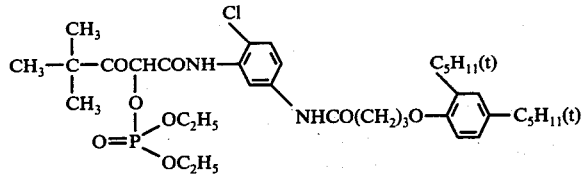
(39)

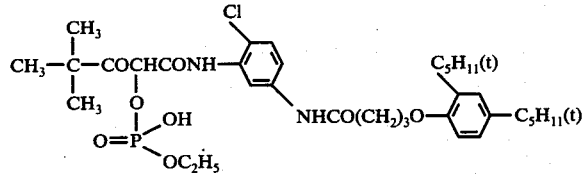
(40)

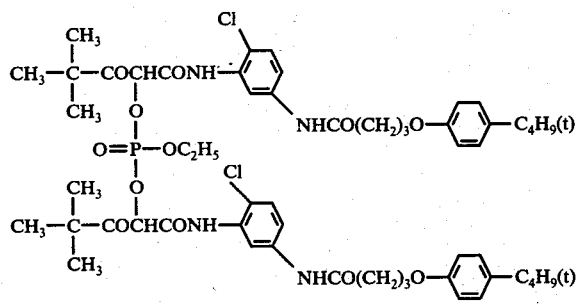
(41)

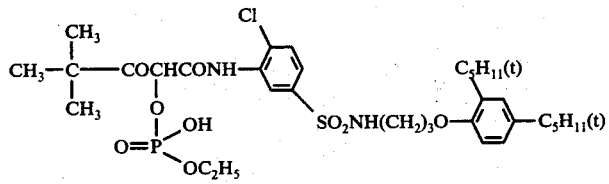
(42)

The couplers according to the present invention can be prepared in the following manner.

Naphthol type couplers can be obtained by mixing a 1,4-dihydroxyaryl compound with a corresponding acid chloride in an equimolar ratio in the presence of a hydrogen chloride removing agent such as pyridine and reacting under cooling or at room temperature, as shown by general formula (XVIII) below. See, in general, G. W. Anderson et al., J. Am. Chem. Soc., 74 5304 (1952). In the case of a phenol type coupler, it is preferred that the hydroxy group at the 1-position be previously protected with an agent such as dihydropyran before reaction with an acid chloride.

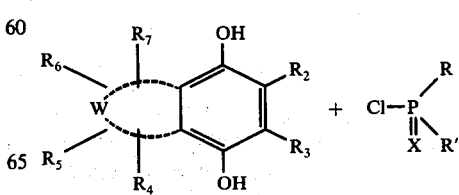

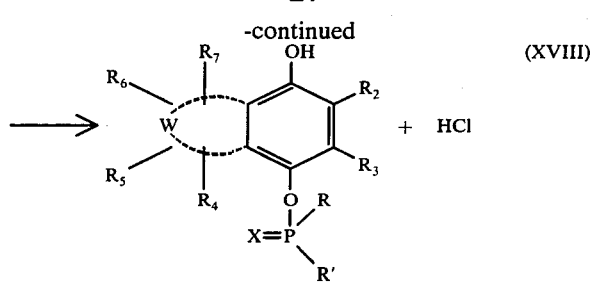

wherein R, R', X, R$_2$, R$_3$, R$_4$, R$_5$, R$_6$, R$_7$ and W each has the same meaning as defined in general formula (XIII).

The pyrazolone or pyrazolobenzimidazole type couplers can be obtained by introducing a hydroxy group at the coupling position and processing in the same manner as described above (see the Anderson citation), as shown by general formula (XIX) below.

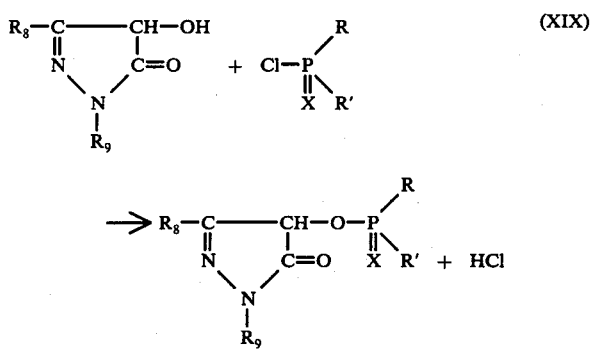

wherein R, R', X, R$_8$ and R$_9$ each has the same meaning as defined in general formula (XIV).

The pivaloylacetanilide type couplers or the benzoylacetanilide type couplers can be obtained by introducing a halogen atom to the coupling position and then reacting it with a metal salt of phosphonic acid in an equimolar ratio in a polar solvent such as N,N-dimethylformamide at a temperature of about 20° to 50° C, as shown by general formula (XX) below. See also U.S. Pat. No. 3,476,563.

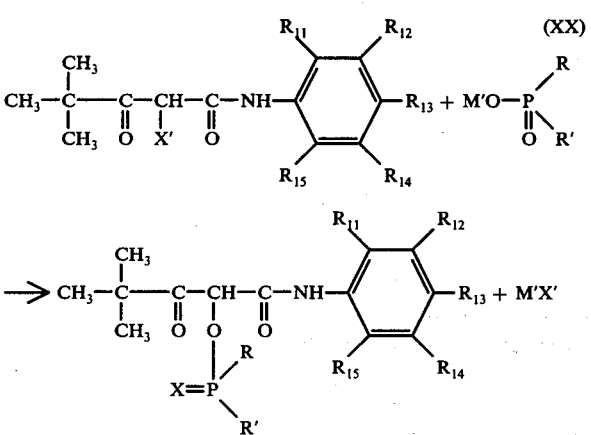

wherein R, R', X, R$_{11}$, R$_{12}$, R$_{13}$, R$_{14}$ and R$_{15}$ each has the same meaning as defined in general formula (XVI); X' represents a bromine atom or a chlorine atom; and M' represents potassium, sodium or silver.

Typical examples of the preparation of the couplers of the present invention are shown in the following.

Unless otherwise indicated, all of the following Synthesis Examples were conducted at atmospheric pressure.

SYNTHESIS EXAMPLE 1

Preparation of 2-chloro-3-methyl-4-diethoxyphosphonyloxy-6-[α-(2,4-di-tert-amylphenoxy)butyramido]phenol [Coupler Example (2)]

14 g of 3-chloro-2-methyl-4-(tetrahydropyran-2-yloxy)-5-[α-(2,4-di-tert-amylphenoxy)butyramido]phenol was dissolved in 70 ml of pyridine, 7.5 g of diethyl chlorophosphate was added thereto under cooling with ice over a period of 30 minutes and the system then stirred for 3 hours at 5° C. The reaction solution was then poured into 500 ml of a 4N aqueous hydrochloric acid solution. The precipitate was extracted with 100 ml of ethyl acetate, washed with water and the solvent distilled off. The residue was dissolved by heating in 150 ml of ethanol and 15 ml of concentrated hydrochloric acid (35 wt%) added thereto and the system then stirred at 50° C for 15 minutes. The resulting solution was cooled with ice and the precipirated crystals were collected and washed with methanol and then water. Upon recrystallization from 150 ml of acetonitrile, 8 g of the desired compound having a melting point of 102° to 103° C was obtained.

SYNTHESIS EXAMPLE 2

Preparation of 1-hydroxy-4-diethoxyphosphonyloxy-N-n-hexadecyl-2-naphthamide [Coupler Example (8)]

10.5 g of 1,4-dihydroxy-N-n-hexadecyl-2-naphthamide was dissolved in 70 ml of pyridine, 7.5 g of diethyl chlorophosphate was added thereto under cooling with ice over a period of 30 minutes and the system then stirred for 3 hours at 5° C. The reaction solution was poured into 500 ml of a 4N aqueous hydrochloric acid solution. The precipitate was extracted with 100 ml of ethyl acetate, washed with water, dried with sodium sulfate and the solvent distilled off. The residue was recrystallized from 50 ml of ethanol to obtain 6 g of the desired compound. The melting point was 95° to 96° C.

SYNTHESIS EXAMPLE 3

Preparation of 1-(2,4,6-trichlorophenyl)-3-{3-[(2,4-di-tert-amylphenoxy)acetamido]benzamido}-4-diethoxyphosphonyloxy-5-pyrazolone [Coupler Example (21)]

3.4 g of 1-(2,4,6-trichlorophenyl)-3-{3-[(2,4-di-tert-amylphenoxy)acetamido]benzamido}-4-hydroxy-b 5-pyrazolone, which was prepared by the method described in Japanese Pat. application 41869/1973, was dissolved in 50 ml of anhydrous ether under a nitrogen atmosphere and 1.5 g of diethyl chlorophosphate was added thereto and the system stirred at room temperature for 5 minutes and then 1.5 g of triethylamine was added thereto. After reaction for 1 hour at room temperature, the precipitated solid was collected by filtration. The solid was added to 30 ml of glacial acetic acid and the acetic acid solution was poured into 200 ml of water. The precipitated white solid was collected by filtration and dried to obtain 2.0 g of the desired compound. The melting point was 105° to 106° C.

SYNTHESIS EXAMPLE 4

Preparation of α-pivaloyl-α-[bis(N,N-dimethylamino)-phosphonyloxy]-2-chloro-5-[α-(2,4-di-tert-amylphenoxy)butyramido]-acetanilide [Coupler Example (34)]

5.7 g of sodium bis(N,N-dimethylamino)phosphorate was dispersed in 100 ml of N,N-dimethylformamide and stirred at 40° C on a water bath for 30 minutes. To the dispersion, a solution containing 19.5 g of α-pivaloyl-α-bromo-2-chloro-5-[α-(2,4-di-tert-amylphenoxy)-butyramido]acetanilide dissolved in 50 ml of N,N-dimethylformamide was added dropwise over a 1 hour period at room temperature. After stirring at 40° C for 1 hour, the reaction solution was poured into 1.5 liters of water. The precipitated oily material was extracted with 300 ml of ethyl acetate, washed with water and dried with sodium sulfate. The ethyl acetate was distilled off and the residue recrystallized from 50 ml of ligroin to obtain 18 g of Coupler (34) having a melting point of 185° to 187° C.

The amount of coupler utilized in accordance with the present invention is not overly important, and is merely selected so as to achieve the desired effect by one skilled in the art. While not to be construed as limitative in any fashion, best results are obtained when about $1 \times 10^{-4}$ to about $1 \times 10^{-3}$ mol/m$^2$ in a photographic paper or about 0.2 to about 50 g/l in a developing solution is utilized. Greater and lesser amounts can be used in both situations, however, without harming the beneficial effects of the present invention.

In order to produce silver halide color photographic light-sensitive materials using the couplers of the present invention, the couplers can be used individually or two or more of the couplers can be used as a mixture. In the color photographic light-sensitive materials containing the couplers of the present invention, other couplers as described below can also be used. For instance, a cyan dye forming coupler such as those described in U.S. Pat. Nos. 2,474,293, 3,034,892, 3,591,383, 3,311,476, 3,476,563, etc., a compound which releases a development inhibitor upon color development (the DIR coupler and DIR compound) such as those described in U.S. Pat. Nos. 3,632,345, 3,227,554, 3,379,529, etc., a yellow dye forming coupler such as those described in German Pat. application (OLS) 2,213,461, U.S. Pat. No. 3,510,306, etc., and a magenta dye forming coupler such as those described in U.S. Pat. No. 3,615,506, Japanese Pat. application 56050/1973, German Pat. application (OLS) 2,418,959, etc.

Two or more of the above described couplers can be used in the same layer so as to achieve the desired characteristics for the light-sensitive material. Alternatively, the same coupler can be added to two or more different layers.

When mixtures of couplers are used to achieve a desired effect, usually the mixture ratio of any coupler will be from about 0.1 mol% to about 99.9 mol%, even more preferably 5 mol% to 95 mol%, of all couplers present.

The silver halide emulsions used in the present invention include silver chloride, silver bromide and mixed silver halides such as silver chlorobromide, silver iodobromide, silver chloroiodobromide, etc. The grains of the silver halide can be in the form of a cubic system, an octahedral system or a mixed crystal system. Uniform grain size is not necessary. The silver halide emulsion can be produced according to known conventional methods, for example, a single or double jet method, a controlled double jet method, etc. Two or more silver halide photographic emulsions previously prepared can also be used as a mixture. Further, the silver halide grains can have a homogeneous crystal structure or a stratum structure wherein the interior and outer portion thereof are different, or can be conversion type grains as described in British Pat. No. 635,841 and U.S. Pat. No. 3,622,318. Furthermore, silver halide grains wherein latent images are formed in the surface portion thereof or those wherein latent images are formed in the interior portion thereof can be used.

The silver halide emulsion can be sensitized with a known chemical sensitizer, for example, sodium thiosulfate, N,N,N'-trimethyl thiourea, aurous thiocyanate complex salt, aurous thiosulfate complex salt, stannous chloride, hexamethylenetetramine, etc., if desired.

Each layer of the photographic light-sensitive material can be applied using various coating methods including dip coating air knife coating, curtain coating, extrusion coating using a hopper as described in U.S. Pat. No. 2,681,294, and simultaneous multilayer coating as described in U.S. Pat. Nos. 2,761,791, 3,508,947, 2,941,898, 3,526,528, etc.

Conventional hydrophilic high molecular weight materials can be used as a binder in the light-sensitive layer of the present invention, for example, gelatin, a cellulose derivative such as carboxymethyl cellulose, hydroxyethyl cellulose, etc., a saccharide derivative such as a starch derivative, etc., a synthetic hydrophilic colloid such as polyvinyl alcohol, poly-N-vinyl pyrrolidone, a copolymer of acrylic acid, polyacrylamide, derivatives thereof or the partially hydrolyzed products thereof, and the like. Of these materials, gelatin is most commonly used. However, portion or all of the gelatin can be replaced by a synthetic high molecular weight material or a gelatin derivative.

The photographic emulsion used in the color photographic light-sensitive material according to the present invention can be spectrally sensitized or supersensitized to blue, green or red light using a cyanine dye such as a cyanine, merocyanine or carbocyanine dye, individually or in combination or using a combination of these dyes and a styryl dye, if desired. Spectral sensitization techniques, for example, those described in U.S. Pat. No. 2,493,748, etc., for blue light sensitization, those described in U.S. Pat. No. 2,688,545, etc., for green light sensitization, those described in U.S. Pat. No. 3,511,664, etc., for red light sensitization, can be used.

Known stabilizing agents and anti-fogging agents, for example, 4-hydroxy-6-methyl-1,3,3a,7-tetraazaindene, 3-methylbenzothiazole, 1-phenyl-5-mercaptotetrazole, a mercury containing compound, a mercapto compound, a metal salt, etc., can be used in the photographic emulsion.

The photographic emulsion layer and other layers of the color light-sensitive material according to the present invention can contain a synthetic polymer compound, for example, a water dispersible vinyl polymer latex such as is described in U.S. Pat. No. 2,376,005, in a hydrophilic colloid such as gelatin, if desired.

The formation of dye images in the present invention can be achieved with various kinds of photographic light-sensitive materials. One process comprises processing a silver halide light-sensitive material with a color developer solution containing an aromatic primary amine color developing agent in which a coupler is dissolved to form a water insoluble or diffusion resistant dye image in the emulsion layer, that is, a coupler-in-developer type color process. For example, Couplers (1), (4), (9), (26) and (27) described above are used in this process. Another process comprises processing a light-sensitive material having on a support a silver halide emulsion layer containing a diffusion resistant coupler with an alkaline developer solution containing an aromatic primary amine color developing agent to form a water insoluble or diffusion resistant dye image in the emulsion layer. For example, Couplers (2), (8), (18), (19), (21) and (37) described above are used in this process. Of these couplers, a colored coupler, for example, Couplers (19) and (20) described above, is used as a masking coupler for compensating undesirable absorption of color image formed in a color photographic material as described, for example, in PSA Journal, Vol. 13, page 94 (1974), or as the so-called diffusible dye releasing coupler which can release a diffusible dye upon coupling reaction with an oxidized aromatic primary amine and form a dye image in an image receiving layer. Still another process comprises processing a light-sensitive photographic material having on a support a silver halide emulsion layer in combination with a diffusion resistant coupler with an alkaline developer solution containing an aromatic primary amine color developing agent to form a diffusible dye which diffuses into an image receiving layer containing a hydrophilic colloid, that is, a diffusion transfer process. For example, Coupler (14) described above, can be used in this process.

The couplers which can be used in the present invention can be dispersed in the photographic emulsion after dissolving them in an aqueous medium or an organic solvent.

Of the couplers of the present invention, oil soluble diffusion resistant couplers which are suitable for use in the coupler-in-emulsion type are incorporated in the light-sensitive material by previously dissolving them in an organic solvent and dispersing the solution in a photographic emulsion as finely divided colloid particles.

Examples of processes for dispersing the couplers of the present invention are described in detail in U.S. Pat. No. 3,676,131. Of the organic solvents used for dissolving couplers, those which are slightly water soluble, which have a high boiling point and which are present with the couplers in the color light-sensitive materials include substituted hydrocarbons, carboxylic acid esters, carboxylic acid amides, phosphoric acid esters and ethers. Specific examples of such compounds are di-n-butyl phthalate, di-isooctyl acetate, di-n-butyl sebacate, tricresyl phosphate, tri-n-hexyl phosphate, N,N-diethylcaprylamide, butyl-n-pentadecylphenyl ether, chlorinated paraffins, etc. In addition to these high boiling point solvents, it is advantageous to use auxiliary solvents which can be removed during production of the light-sensitive materials in order to assist the dissolution of the couplers. Examples of such compounds are propylene carbonate, ethyl acetate, butyl acetate, cyclohexanol, tetrahydrofuran, cyclohexanone, etc.

It is advantageous to use a surface active agent for the purpose of finely dispersing the oil soluble coupler-in-emulsion type coupler in a hydrophilic high molecular weight material used for a photographic emulsion. It is particularly preferred to use an anionic surface active agent such as sodium cetyl sulfate, sodium p-dodecylbenzene sulfonate, sodium nonylnaphthalene sulfonate, sodium di(2-ethylhexyl)-α-sulfosuccinate, etc., and a nonionic surface active agent such as sorbitan sesquioleic acid ester, sorbitan monolauric acid ester, etc.

A homogenizer for emulsification, a colloid mill, an ultrasonic emulsification device, etc., are useful for dispersing oil soluble couplers. Diffusion resistant couplers having a carboxylic acid group or a sulfonic acid group together with a ballast group in the molecule are soluble in a neutral or weak alkaline aqueous solution. By adding such an aqueous solution containing the coupler to a photographic emulsion, the coupler can be incorporated into the photographic emulsion. It is believed that the coupler becomes diffusion resistant due to the formation of micelles in the hydrophilic high molecular weight material.

Silver halide light-sensitive materials to which the coupler of the present invention is applicable include not only conventional color light-sensitive materials such as a color negative film, a color positive film, a color reversal film, a color paper, etc., but also other various color light-sensitive materials. For examples, they include a color direct positive light-sensitive material, a monochromatic light-sensitive material, a light-sensitive material for color radiography, an instant color light-sensitive material such as those for a color diffusion transfer process, etc.

The coupler of the present invention can be used in known multilayer structures of a multilayer color light-sensitive material, for example, those described in U.S. Pat. Nos. 3,726,681 and 3,516,831, British Pat. Nos. 818,687 and 923,045, in a method as described in Japanese Patent Application 5179/1975, and in a method in which the coupler is used together with a DIR compound as described in German Patent Application (OLS) 2,322,165 and U.S. Pat. No. 3,703,375.

The coupler is generally used in the amount of 10 to 1,500 g per mol of silver halide. However, the amount can be varied therefrom according to the end use purpose.

The silver halide light-sensitive material used in the present invention comprises a support having coated thereon various photographic layers such as a silver halide emulsion layer, an intermediate layer, an antihalation layer, a protective layer, a yellow filter layer, a backing layer, a mordanting polymer layer, a layer for preventing contamination with a developer, etc. The color silver halide emulsion layers comprise a red-sensitive layer, a green-sensitive layer and a blue-sensitive layer. The order of these layers is not fixed, and each layer can be divided into two or more layers.

It is advantageous, to increase the stability of the color photographic images formed, that the light-sensitive material of the present invention contain a p-substituted phenol derivative in an emulsion layer thereof or an adjacent layer thereto. Particularly preferred p-substituted phenol derivatives are a hydroquinone derivative as described in U.S. Pat. Nos. 2,360,290, 2,418,613, 2,675,314, 2,701,197, 2,704,713, 2,710,801, 2,728,659, 2,732,300, 2,735,765 and 2,816,028, a gallic acid derivative as described in U.S. pat. Nos. 3,457,079 and 3,069,262 and Japanese Patent Publication 13496/1968, a p-alkoxyphenol as described in U.S. Pat. No. 2,735,765 and Japanese Pat. application (OPI) 4738/1972, and a p-oxyphenol derivative as described in U.S.. Pat. Nos. 3,432,300, 3,573,050, 3,574,627 and 3,764,337.

The light-sensitive material used in the present invention preferably contains an ultraviolet absorbing agent as described, for example, in U.S. Pat. Nos. 3,250,617 and 3,253,921, in an emulsion layer or a layer adjacent thereto so as to stabilize the images formed.

Hardening of the emulsion layer can be carried out in a conventional manner, if desired or necessary. Examples of hardening agents include an aldehyde type compound such as formaldehyde, glutaraldehyde, etc., a ketone compound such as diacetyl, cyclopentanedione, etc., a reactive halogen containing compound such as bis(2-chloroethylurea), 2-hydroxy-4,6-dichloro-1,3,5- triazine, a compound as described in U.S. Pat. Nos. 3,288,775, 2,732,303, 3,125,449 and 1,167,207, etc., a reactive olefin containing compound such as divinyl sulfone, 5-acetyl-1,3-diacryloylhexahydro-1,3,5-triazine, a compound as described in U.S. Pat. Nos. 3,635,718 and 3,232,763 and British Pat. No. 994,869, etc., an N-methylol compound such as N-hydroxymethyl phthalimide, a compound as described in U.S. Pat. Nos. 2,732,316 and 2,586,168, etc., an isocyanate such as described in U.S. Pat. No. 3,103,437, etc., an aziridine compound such as is described in U.S. Pat. Nos. 3,017,280 and 2,983,611, etc., an acid derivative such as is described in U.S. Pat. Nos. 2,725,294 and 2,725,295, etc., a carbodiimide type compound such as is described in U.S. Pat. No. 3,100,704, etc., an epoxy compound such as described in U.S. Pat. No. 3,091,537, etc., an isoxazole type compound such as described in U.S. Pat. Nos. 3,321,313 and 3,543,292, etc., a halogenocarboxyaldehyde such as mucochloric acid, etc., a dioxane derivative such as dihydroxydioxane, dichlorodioxane, etc., and an organic hardening agent such as chromium alum, zirconium sulfate, etc. Further, a precursor compound, for example, an alkali metal bisulfite aldehyde addition product, a methylol derivative of hydantoin, a primary aliphatic nitroalcohol, etc., can be used instead of the above described compound.

The support for the color light-sensitive material of the present invention can be freely selected from those as are generally used in the art and includes a cellulose nitrate film, a cellulose acetate film, a cellulose acetate butyrate film, a polystyrene film, a polyethylene terephthalate film, a polycarbonate film, a laminate of these films, a thin glass film, a paper, a paper coated or laminated with baryta or an α-olefin polymer, particularly a polymer of α-olefin having 2 to 10 carbon atoms, such as polyethylene, polypropylene, an ethylenebutene copolymer, etc., a plastic film whose surface has been roughened so as to improve adhesion to other high molecular weight materials and to improve printability as described in Japanese Patent Publication 19068/1972, and the like.

When the adhesive strength between the support and the photographic emulsion layer is insufficient, a subbing layer which is adhesive to both the support and the photographic emulsion layer can be employed. Further, the surface of the support can be subjected to a pretreatment such as a corona discharge, an ultraviolet irradiation treatment, a flame treatment, etc., for the purpose of further improving adhesion.

The color photograhic light-sensitive material of the present invention can be subjected, after exposure, to a processing basically including a color development, a bleaching and a fixing. Each step can be conducted separately or two or more steps can be carried out as one step using a processing solution which has the functions for these steps. The use of a mono-bath-bleach-fixing solution is one example thereof. If desired, the processing can include other steps such as a prehardening, a neutralization, a first development (black-and-white development), an image stabilizing, a water washing, etc.

The processing temperature is selected depending on the kind of light-sensitive material and method of processing. The processing temperature is sometimes below 18° C but often above 18° C. Particularly, the temperature ranges from 20° to 60° C. The temperature of each step need not necessarily be the same.

A color developer solution is an alkaline aqueous solution having a pH of above 8 and particularly 9 to 12 which contains a color developing agent.

Preferred examples of the above described color developing agent are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline, and salts thereof (for example, the sulfate, hydrochloride, sulfite, p-toluene-sulfonate, etc.). In addition, the compounds described in U.S. Pat. Nos. 2,193,015, and 2,592,364, Japanese Patent Application (OPI) 64933/1973 and L.F.A. Mason, Photographic Processing Chemistry, pages 226 to 229, Focal Press, London (1966), can be used.

Further, the above described compounds can be used together with a 3-pyrazolidone. Various known additives can be added to the color developer solution, if desired.

After color development, the light-sensitive material of the present invention is subjected to bleaching in a conventional manner. The bleaching can be carried out separately or simultaneously with fixing. It is, thus, possible, if desired, to add a fixing agent to the bleaching solution to make a bleach-fixing bath. Many compounds can be used as a bleaching agent. For example, a ferricyanide, a bichromate, a water soluble cobalt (III) salt, a water soluble copper (II) salt, a water soluble quinone, a nitrosophenol, a polyvalent metal compound such as iron (III), a cobalt (III), copper (II), etc., and, particularly, a complex salt of such a polyvalent metal cation and an organic acid, for example, a metal complex salt of an aminopolycarboxylic acid such as ethylenediamine tetraacetic acid, nitrilotriacetic acid, iminodiacetic acid, N-hydroxyethyl ethylenediamine triacetic acid, etc., malonic acid, tartaric acid, malic acid, diglycolic acid, dithioglycolic acid, etc., and a 2,6-dipicoline copper complex salt, etc., a peracid, for example, an alkyl peracid, a persulfate, a permanganate, hydrogen peroxide, etc., a hypochlorite, bleaching powder, etc., can be used, individually or as a suitable combination thereof. It is also possible to add to this processing solution a bleaching accelerating agent as described in U.S. Pat. Nos. 3,042,520 and 3,241,966, Japanese Pat. Publications 8506/1970 and 8836/1970, etc., and other various additives.

The coupler of the present invention can be used for light-sensitive materials having a low silver content wherein the amount of silver halide in an emulsion is from one half to one hundredth of that in conventional light-sensitive materials. In case of using such color light-sensitive materials having a low silver halide content, for example, the coating amount of silver halide being 3.3 mg/dm$^2$ or less, it is possible to utilize an image forming process which comprises a color intensification using a peroxide or a cobalt complex salt, for example, as described in German Pat. application (OLS) 2,357,694, U.S. Pat. Nos. 3,674,490 and 3,761,265, German Patent Applications 2,044,833, 2,056,359, 2,056,360, 2,226,770, Japanese Pat. Applications (OPI) 9728/1973 and 9729/1973, etc., so as to obtain a sufficient color image density.

The present invention will be further illustrated by the following Examples. However, the present invention is not to be construed as being limited to these Examples. In the following Examples, all percentages, parts and the like are by weight, unless otherwise indicated.

EXAMPLE 1

To 10 g of the above described Coupler (8), 1-hydroxy-4-diethoxyphosphonyloxy-N-n-hexadecyl-2-naphthamide, 10 ml of di-n-butylphthalate and 20 ml of ethyl acetate were added and the system heated at 50° C to dissolve. The solution was added to 100 ml of an aqueous solution containing 10 g of gelatin and 0.5 g of sodium p-dodecylbenzene sulfonate and the mixture mechanically stirred using a high speed agitator for 20 minutes, thereby giving a fine dispersion of the coupler together with the solvent.

63.5 g of the fine dispersion was added to 100 g of a photographic emulsion containing 0.03 mol of silver chlorobromide (containing 50 mol% of bromide) and 8 g of gelatin, then 12 ml of a 2% aqueous solution of 2-hydroxy-4,6-dichloro-s-triazine sodium salt was added as a hardener. The pH of the mixture was adjusted to 6.0 and the mixture was applied to a cellulose triacetate film base at a silver coated amount of $90 \times 10^{-6}$ g/cm$^2$ to prepare a photographic light-sensitive material. This material is designated Sample A. The coupler content of Sample A was $2.10 \times 10^{-3}$ mol/m$^2$.

For comparison, a photographic light-sensitive material was prepared using the same procedure as described for Sample A except that 10 g of 1-hydroxy-4-chloro-N-n-hexadecyl-2-naphthamide [Coupler (a)] was used in place of Coupler (8) and 50.5 g of the coupler dispersion was used. This material is designated Sample B. The coupler content of Sample B was $2.16 \times 10^{-3}$ mol/m$^2$.

These photographic light-sensitive materials were subjected to sensitometric stepwise exposure followed by processing in the following sequence.

| | Temperature (° C) | Time (minute) |
|---|---|---|
| 1. Color Development | 24 | 8 |
| 2. Washing | " | 1 |
| 3. First Fixing | " | 4 |
| 4. Washing | " | 10 |
| 5. Bleaching | " | 6 |
| 6. Washing | " | 3 |
| 7. Second Fixing | " | 4 |
| 8. Washing | " | 10 |

The composition of the color developer solution used in the processing was as follows:

| Color Developer Solution | | |
|---|---|---|
| Sodium sulfite (anhydrous) | 3.0 | g |
| 4-Amino-3-methyl-N,N-diethylaniline hydrochloride | 2.5 | g |
| Sodium carbonate (monohydrate) | 47.0 | g |
| Potassium bromide | 2.0 | g |
| Water to make | 1,000 | ml |

The fixing solution and the bleaching solution each had the following composition.

| Fixing Solution (first and second fixing solution) | | |
|---|---|---|
| Sodium thiosulfate | 150 | g |
| Sodium sulfite | 15 | g |
| Glacial acetic acid (28% aq. soln.) | 48 | ml |
| Boric acid | 7.5 | g |
| Water to make | 1,000 | ml |
| Bleaching Solution | | |
| Potassium bromide | 20 | g |
| Potassium ferricyanide | 100 | g |
| Glacial acetic acid | 20 | ml |
| Sodium acetate | 40 | g |
| Water to make | 1,000 | ml |

After the processing, the optical density of Samples A and B to red light was measured to obtain the results shown in Table 1.

TABLE 1

| Film Sample | Coupler | Coupler Coated Amount (mol/m$^2$) | Fog | Sensitivity* (relative value) | Gamma | Maximum Density |
|---|---|---|---|---|---|---|
| A | (8) | $2.10 \times 10^{-3}$ | 0.05 | 100 | 3.22 | 3.40 |
| B | (a) | $2.16 \times 10^{-3}$ | 0.05 | 93 | 2.20 | 3.18 |

*Amount of exposure required to give a density of fog + 0.10.

With Samples A and B, the maximum densities to red light which were obtained upon processing for different periods of developing time are shown in Table 2.

TABLE 2

| Film Sample | Coupler | Developing Time (min) | | |
|---|---|---|---|---|
| | | 4 | 8 | 15 |
| A | (8) | 3.31 | 3.40 | 3.42 |
| B | (a) | 2.90 | 3.18 | 3.30 |

These results show that the coupler in which the active position is substituted with a diethoxyphosphonyloxy group used in the present invention can give higher sensitivity, gradation and color density, in comparison with those of a coupler in which the active position is substituted with a chlorine atom such as Coupler (a), and also give sufficient color image formation within a short period of time, thus making it possible to shorten the processing time.

When the above described Coupler (10) was used in place of the above described Coupler (8) and the same procedure was repeated, high sensitivity, gradation and color density were again obtained. In this case the superiority of the coupler of the present invention to the coupler in which the active position is substituted with a chlorine atom was also recognized.

In order to confirm this improved coupling reactivity the following experiment was carried out.

The above described Couplers (8) and (10) and Coupler (a) each was admixed with a yellow forming Coupler (b), i.e., α-(4-methoxybenzoyl)-2-chloro-5-[α-(2,4-di-tert-amylphenoxy)-butyramido]acetanilide, in a molar ratio of 1 : 2 and competing color development, using 4-amino-3-methyl-N,N-diethylaniline as a color developing agent, was carried out. Analysis of the ratio of the formed cyan dye to the yellow dye was performed from which the relative value, based on the yellow forming Coupler (b), of the reaction rate constant in the reaction of the coupler of the present invention was calculated. The relative value of the reaction rate constant was determined by measuring the amounts of two dyes in the color images obtained by mixing two couplers M and N which give clearly separated different colors and adding the mixture to an emulsion, and then performing color development. If coupler M provides color of the maximum density (DM)max and color of density DM in an intermediate stage, and coupler N provides colors of (DM)max and DN, respectively, the ratio RM/RN of the reaction activities of both couplers is expressed by the following equation.

$$\frac{RM}{RN} = \frac{\log\left(1 - \frac{DM}{(DM)\max}\right)}{\log\left(1 - \frac{DN}{(DN)\max}\right)}$$

That is, the coupling activity ratio RM/RN can be obtained from the gradient of the straight line which is obtained by plotting several sets of DM and DN resulting from imparting several stages of exposure to an emulsion containing mixed couplers and subjecting them to color development, on two axes crossing at right angles to each other as $\log(1 - (D/D\max))$.

Coupler (8) and Coupler (10) in which the active position is substituted with a phosphonyloxy group gave a relative rate constant of 1.4 and 1.6, respectively, while known Coupler (a), in which the active position is substituted with a chlorine atom, gave a relative rate constant of 1.2. These results clearly indicate that the couplers of the present invention have improved reactivity and are superior couplers.

EXAMPLE 2

To 10 g of the above described Coupler (7), 1-hydroxy-4-ethoxy-(phenoxy)-phosphonyloxy-N-[γ-(2,4-di-tert-amylphenoxy)-propyl]-2-naphthamide, 10 ml of tricresyl phosphate, 20 ml of ethyl acetate and 0.5 g of sodium di(2-ethylhexyl)-α-sulfosuccinate were added and the system heated at 50° C to dissolve. The mixture was added to 100 ml of an aqueous solution containing 10 g of gelatin and finely dispersed using a homogenizer.

43.5 g of this fine dispersion was added to 100 g of a silver iodobromide emulsion (containing 7 mol% of iodide, $3.5 \times 10^{-2}$ mol of silver and 6 g of gelatin). 5 ml of a 2% methanol solution of 5-methyl-7-hydroxy-1,3,4,7a-tetraazaindene and 9.0 ml of a 2% aqueous solution of 2-hydroxy-4,6-dichloro-s-triazine sodium salt were then added to the mixture. After adjusting the pH to 6.5, the mixture was coated on a cellulose triacetate base in a coated amount of coupler of $2.0 \times 10^{-3}$ mol/m². This was designated Sample C.

For comparison, using each of Coupler (c) and Coupler (d), both having the same structure but the coupling position, being unsubstituted in Coupler (c) and substituted with a chlorine atom in Coupler (d), fine dispersions were prepared in the same manner as described above. 31 g of the coupler dispersion containing the unsubstituted coupler was added to 200 g of the same emulsion as above and 33 g of the coupler dispersion containing the chloro-substituted coupler was added to 100 g of the same emulsion as above and the same stabilizing agent and hardening agent were added thereto in an amount corresponding to the amount of silver and gelatin contained to prepare Sample D and Sample E. The coupler contents of these Samples were $2.10 \times 10^{-3}$ mol/m² and $2.04 \times 10^{-3}$ mol/m², respectively.

These three Samples were subjected to sensitometric stepwise exposure and processed in the following manner.

| Processing Step | Temperature (° C) | Time (minutes) |
|---|---|---|
| 1. Color Development | 38 | 3 |
| 2. Stopping | " | 1 |
| 3. Washing | " | 1 |
| 4. Bleaching | " | 2 |
| 5. Washing | " | 1 |
| 6. Fixing | " | 2 |
| 7. Washing | " | 1 |
| 8. Stabilizing | " | 1 |

The compositions of the processing solutions used were as follows.

| Color Developer Solution | | |
|---|---|---|
| Sodium hydroxide | 2 | g |
| Sodium sulfite | 2 | g |
| Potassium bromide | 0.4 | g |
| Sodium chloride | 1 | g |
| Borax | 4 | g |
| Hydroxylamine sulfate | 2 | g |
| Disodium ethylenediamine tetraacetate (dihydrate) | 2 | g |
| 4-Amino-3-methyl-N-ethyl-N-(β-hydroxyethyl)aniline monosulfate | 4 | g |
| Water to make | 1,000 | ml |
| Stopping Solution | | |
| Sodium thiosulfate | 10 | g |
| Ammonium thiosulfate (70% aq. soln.) | 30 | ml |
| Glacial acetic acid | 30 | ml |
| Sodium acetate | 5 | g |
| Potassium alum | 15 | g |
| Water to make | 1,000 | ml |
| Bleaching Solution | | |
| Sodium iron (III) ethylenediamine tetraacetate (dihydrate) | 100 | g |
| Potassium bromide | 50 | g |
| Ammonium nitrate | 50 | g |
| Boric acid | 5 | g |
| Aqueous ammonia to adjust pH to 5.0 | | |
| Water to make | 1,000 | ml |
| Fixing Solution | | |
| Sodium thiosulfate | 150 | g |
| Sodium sulfite | 15 | g |
| Borax | 12 | g |
| Glacial acetic acid | 15 | ml |
| Potassium alum | 20 | g |
| Water to make | 1,000 | ml |
| Stabilizing Bath | | |
| Boric acid | 5 | g |
| Sodium citrate | 5 | g |
| Sodium metaborate (tetrahydrate) | 3 | g |
| Potassium alum | 15 | g |
| Water to make | 1,000 | ml |

After the processing, the optical density of Samples C, D and E to red light was measured to obtain the results shown in Table 3.

TABLE 3

| Film Sample | Coupler | Coupler Coated Amount (mol/m²) | Fog | Sensitivity* (relative value) | Gamma | Maximum Density |
|---|---|---|---|---|---|---|
| C | (7) | $2.00 \times 10^{-3}$ | 0.07 | 100 | 2.35 | 2.42 |
| D | (c) | $2.10\ 33\ 10^{-3}$ | 0.07 | 87 | 1.70 | 2.33 |

TABLE 3-continued

| Film Sample | Coupler | Coupler Coated Amount (mol/m²) | Fog | Sensitivity* (relative value) | Gamma | Maximum Density |
|---|---|---|---|---|---|---|
| E | (d) | 2.04 × 10⁻³ | 0.07 | 89 | 1.88 | 2.29 |

*Amount of exposure required to give a density of fog + 0.10.

These results show that the coupler in which the active position is substituted with a phosphonyloxy group used in the present invention gives higher sensitivity, gradation and maximum density, in comparison with couplers used in the Comparison Samples, i.e., Coupler (c) in which the active position is unsubstituted and Coupler (d) in which the active position is substituted with a chlorine atom. Further, no degradation in graininess of the color image due to the increase in coupling reactivity was observed upon microscopic examination.

EXAMPLE 3

A mixture of 36.7 g of the above described Coupler (2), 2-chloro-3-methyl-4-diethoxyphosphonyloxy-6-[α-(2,4-di-tert-amylphenoxy)butyramido]phenol, 40 ml of tri-n-hexyl phosphate, 80 ml of ethyl acetate and 2.0 g of sodium di-(2-ethylhexyl)-α-sulfosuccinate was dissolved by heating at 50° C. The solution was added to 400 ml of an aqueous solution containing 40 g of a gelatin and stirred and then finely dispersed by a homogenizer.

To 1.0 kg of a silver chlorobromide emulsion containing 50 mol% of bromide, 0.3 mol of silver and 70 g of gelatin, 200 ml of a 0.01% methanol solution of Compound I-6 described in Japanese Patent Publication 22189/1970, as a red-sensitive sensitizing dye and 50 ml of a 1% methanol solution of 5-methyl-7-hydroxy-1,3,4,7a-tetraazaindene were added.

To the emulsion all of the above described dispersion was added and then 30 ml of a 3% acetone solution of triethylene phosphamide was added as a hardener. The pH of the mixture was adjusted to 6.5 to prepare a red-sensitive silver halide emulsion.

On a baryta paper resin-coated with polyethylene on both surfaces were coated, as a first layer, a blue-sensitive silver halide emulsion containing Coupler (e), α-(5,5-dimethyl-2,4-dioxooxazolidin-3-yl)-α-pivaloyl-2-chloro-5-[α-(2',4'-di-tert-amylphenoxy)butyramido]-acetanilide in a dry thickness of 4.0 microns, as a second layer, a gelatin solution in a dry thickness of 1.0 micron, as a third layer, a green-sensitive silver halide emulsion containing Coupler (f), 1-(2,4,6-trichlorophenyl)-3-[(2-chloro-5-n-tetradecanamido)anilino]-5-pyrazolone in a dry thickness of 2.5 microns, as a fourth layer, a gelatin solution containing 2-(2'-benzotriazolyl)-4,6-dibutyl-phenol, as an ultraviolet absorber, in a dry thickness of 2.5 microns, as a fifth layer, the above described red-sensitive silver halide emulsion in a dry thickness of 3.5 microns, and as an uppermost layer, a gelatin solution in a dry thickness of 0.5 micron, thus preparing a color print paper.

This color print paper was optically printed using a color negative and processed in the following manner.

| Processing Step | Temperature (° C) | Time (minute) |
|---|---|---|
| 1. Color Development | 30 | 6 |
| 2. Stopping | " | 2 |
| 3. Washing | " | " |
| 4. Blixing | " | " |
| 5. Washing | " | " |
| 6. Stabilizing | " | " |

The compositions of the processing solutions used were as follows.

| Color Developer Solution | | |
|---|---|---|
| Benzyl alcohol | 12 | ml |
| Diethylene glycol | 3.5 | ml |
| Sodium hydroxide | 2.0 | g |
| Sodium sulfite | 2.0 | g |
| Potassium bromide | 0.4 | g |
| Sodium chloride | 1.0 | g |
| Borax | 4.0 | g |
| Hydroxylamine sulfate | 2.0 | g |
| Disodium ethylenediamine tetraacetate (dihydrate) | 2.0 | g |
| 4-Amino-3-methyl-N-ethyl-N-(β-methanesulfonamidoethyl)aniline sesquisulfate (monohydrate) | 5.0 | g |
| Water to make | 1,000 | ml |
| Stopping Solution | | |
| Sodium thiosulfate | 10 | g |
| Ammonium thiosulfate (70%) | 30 | ml |
| Sodium acetate | 5 | g |
| Glacial acetic acid | 30 | ml |
| Potassium alum | 15 | g |
| Water to make | 1,000 | ml |
| Blixing Solution | | |
| Ferric sulfate | 20 | g |
| Disodium ethylenediamine tetraacetate (dihydrate) | 36 | g |
| Sodium carbonate (monohydrate) | 17 | g |
| Sodium sulfite | 5 | g |
| Ammonium thiosulfate (70%) | 100 | ml |
| Boric acid | 5 | g |
| pH adjusted to 6.8 | | |
| Water to make | 1,000 | ml |
| Stabilizing Solution | | |
| Boric acid | 5 | g |
| Sodium citrate | 5 | g |
| Sodium metaborate (tetrahydrate) | 3 | g |
| Potassium alum | 15 | g |
| Water to make | 1,000 | ml |

The resulting color print was a sharp color image having excellent color reproducibility. The cyan dye image had an absorption maximum at 673 millimicrons.

Further, when this color print was exposed to a white light fluorescent lamp of 30,000 lux for 20 days, the reduction of density of the cyan dye image having an initial reflection density of 1.0 was only 0.02, and when it was allowed to stand under high temperature and high humidity conditions, i.e., at 60° C and 75% RH for 20 days, the reduction of density of the cyan dye image having an initial reflection density of 1.0 was only 0.12. These results show excellent image stability.

Also, unexposed samples were stored under the conditions of 40° C and 80% RH for 2 days and under the conditions of 25° C and 60% RH for 2 days, subjected to sensitometric stepwise exposure and processed in the above described manner. The results indicate that the photographic material is stable and shows a small change in photographic properties such as maximum density, fog, gamma, etc., even though it was stored under severe conditions.

EXAMPLE 4

A mixture of 15 g of the above described Coupler (3), 2-(2,2,3,3,4,4,5,5-octafluorovaleramido)-4-[ethoxy(4-nitrophenoxy)-phosphonyloxy]-5-[α-(2,4-di-tert-amyl-phenoxy)butyramido]phenol, 15 ml of tricresyl phosphate and 30 ml of ethyl acetate was dissolved by heating at 50° C. The solution was added to 150 ml of an aqueous solution containing 0.75 g of sodium p-dodecylbenzene sulfonate and 15 g of gelatin, stirred and subjected to vigorous mechanical stirring. The coupler was finely dispersed together with the solvent.

All of the coupler dispersion was added to 100 g of a silver iodobromide emulsion for a reversal film containing 3 mol% of iodide, $3.5 \times 10^{-2}$ mol of silver and 7.0 g of gelatin to which 14 ml of a 4% aqueous solution of 2-hydroxy-4,6-dichloro-s-triazine sodium salt was added as a hardener. The pH of the mixture was adjusted to 7.0 and then the mixture was coated on a polyethylene terephthalate film base in a silver coated amount of 0.90 g/m².

The sample thus prepared was subjected to sensitometric stepwise exposure followed by processing in the following manner.

| Processing step | Temperature (° C) | Time (minute) |
|---|---|---|
| 1. First Development | 30 | 3 |
| 2. Washing | " | 0.5 |
| 3. Reversal Exposure | uniform exposure of 8,000 lux.sec to the emulsion surface | |
| 4. Second Development | 30 | 4 |
| 5. Washing | " | 1 |
| 6. Bleaching | " | 1 |
| 7. Washing | " | 0.5 |
| 8. Fixing | " | 1 |
| 9. Washing | " | 1 |

The compositions of the processing solutions used were as follows.

| First Developer Solution | | |
|---|---|---|
| 4-(N-Methylamino)phenol sulfate | 2 | g |
| Sodium sulfite | 90 | g |
| Hydroquinone | 8 | g |
| Sodium carbonate (monohydrate) | 52.5 | g |
| Potassium bromide | 5 | g |
| Potassium thiocyanate | 1 | g |
| Water to make | 1,000 | ml |
| Second Developer Solution | | |
| Benzyl alcohol | 5 | ml |
| Sodium sulfite | 5 | g |
| Hydroxylamine hydrochloride | 2 | g |
| 4-Amino-3-methyl-N-ethyl-N-(β-ethoxyethyl)-aniline p-toluenesulfonate | 3 | g |
| Potassium bromide | 1 | g |
| Trisodium phosphate | 30 | g |
| Sodium hydroxide | 0.5 | g |
| Ethylenediamine (70% aq. soln.) | 7 | ml |
| Water to make | 1,000 | ml |
| Bleaching Solution | | |
| Potassium ferricyanide | 160 | g |
| Potassium bromide | 40 | g |
| Borax | 1 | g |
| Water to make | 1,000 | ml |
| Fixing Solution | | |
| Sodium thiosulfate | 150 | g |
| Sodium acetate | 70 | g |
| Sodium sulfite | 10 | g |
| Potassium alum | 20 | g |
| Water to make | 1,000 | ml |

The reversal color image thus obtained had clear color with an absorption maximum at 672 millimicrons and exhibited excellent color.

Further, another sample was stored at 40° C, 75% RH for 3 days and subjected to sensitometric stepwise exposure and the above described processing. The results were compared with those obtained above and no substantial differences in photographic properties such as maximum density, fog, gamma, sensitivity, etc., were observed. It is clear that the coupler of the present invention has superior stability.

Moreover, when the color image thus obtained was allowed to stand at high temperature and high humidity conditions, i.e., at 60° C and 75% RH for 20 days, the reduction of density of the cyan image having an initial transmittance density of 1.0 was only 0.05. The results show excellent image stability.

EXAMPLE 5

A multilayer color light-sensitive material was prepared by coating a first layer to a ninth layer each having the following composition on a transparent cellulose triacetate film base.

First Layer: Antihalation Layer

To 1 kg of a 5% aqueous gelatin solution containing black colloidal silver, 25 ml of a 4% aqueous solution of 2,6-dichloro-4-hydroxy-s-triazine sodium salt (designated Hardener (I) was added). The mixture was coated in a dry thickness of 1.0 micron.

Second Layer: Intermediate Layer 50 g of 2,5-di-tert-octylhydroquinone was dissolved in 100 ml of tricresyl phosphate and 200 ml of ethyl acetate and added to 1.0 liter of an aqueous solution containing 100 g of gelatin and 5.0 g of sodium dioctyl sulfosuccinate and mechanically vigorously stirred using a high speed stirrer to prepare a dispersion. 250 g of the thus prepared dispersion (Dispersion I) was mixed with 1.0 liter of an aqueous solution containing 100 g of gelatin and to which 25 ml of a 4% aqueous solution of Hardener (I) was added. The mixture was coated in a dry thickness of 1.0 micron.

Third Layer: Red-Sensitive Emulsion Layer

A coating solution was prepared in the following manner and coated.

1.0 kg of a silver iodobromide emulsion prepared in a conventional manner (0.5 mol of silver, 7 mol% of iodide, 62 g of gelatin, mean grain size of 0.4 micron) was spectrally sensitized with $5 \times 10^{-5}$ mol per mol of silver of anhydro-5,5'-dichloro-3,3'-disulfopropyl-9-ethyl-thiacarbocyanine hydroxide pyridinium salt and $1.2 \times 10^{-5}$ mol per mol of silver of anhydro-9-ethyl-3,3'-di(3-sulfopropyl)-4,5,4',5'-dibenzothiacarbocyanine hydroxide triethylamine salt, as red-sensitive sensitizing dyes to form a "red-sensitive emulsion."

Separately therefrom, 83 g of Coupler (7), 1-hydroxy-4-ethoxy(phenoxy)phosphonyloxy-N-[γ-(2,4-di-tert-amylphenoxy)-propyl]-2-naphthamide, 3.5 g of Coupler (g), 1-hydroxy-4-(4-ethoxycarbonylphenylazo)-N-dodecyl-2-naphthamide and 11 g of Coupler (h), α-(4-octadecyloxybenzoyl)-α-[5-(3-methyl-2-benzo-thiazolinidenamino)-1-benzotriazolyl]-2-ethoxyacetanilide were dissolved in 100 ml of tricresyl phosphate and 150 ml of ethyl acetate and Dispersion II was prepared in the same manner as preparing Dispersion I of the second layer. 780 g of Dispersion II was added to the above described "red-sensitive emulsion", to which 23 ml of a 4% aqueous solution of Hardener (I) was then added. The mixture was coated in a silver coated amount of 1.2 g/m².

Fourth Layer: Magenta Colored Coupler Layer 77.5 ml of a 5% alkaline aqueous solution (containing 0.1N of sodium hydroxide) of the above described Coupler (19), 1-hydroxy-4-ethoxy-{β-[4-(1-hydroxy-3,6-disulfo-8-acetamido-2-naphthylazo)phenoxy]ethoxy}-phosphonyloxy-N-n-hexadecyl-2-naphthamide disodium salt, was added to 1 liter of an aqueous solution containing 100 g of gelatin and to which 27 ml of a 2% aqueous solution of citric acid, 250 g of Dispersion I used in the second layer and 25 ml of a 4% aqueous solution of Hardener (I) were added. The mixture was coated in a dry thickness of 1.5 microns.

Fifth Layer: Intermediate Layer

The coating solution as described in the second layer was coated in a dry thickness of 1.0 micron.

Sixth Layer: Green-Sensitive Emulsion Layer

A green-sensitive emulsion was prepared by adding 2 $\times$ 10$^{-4}$ mol of anhydro-9'-ethyl-5,5'-dichloro-3,3'-disulfopropyloxacarbocyanine sodium salt and 6 $\times$ 10$^{-5}$ mol of anhydro-5,6,5',6'-tetrachloro-1,1'-diethyl-3,3'-disulfopropoxyethylimidazolocarbocyanine hydroxide sodium salt, as green-sensitive sensitizing dyes, to 1.0 kg of the same silver iodobromide emulsion as was used in the third layer. 80 g of the above described Coupler (21), 1-(2,4,6-trichlorophenyl)-3-{3-[2,4-di-tert-amylphenoxy)acetamido]benzamido}-4-diethoxyphosphonyloxy-5-pyrazolone, 7.5 g of Coupler (i), 1-(2,4,6-trichlorophenyl)-3-(2-chloro-5-tetradecanamidoanilino)-4-(3-methyl-4-hydroxy-phenylazo)-5-pyrazolone and 8.5 g of Coupler (j), 1-benzyl-3-(2-chloro-5-tetradecanamidoanilino)-4-(2- or 4-octanamido-1-benzotriazolyl)-5-pyrazolone, were dissolved in 100 ml of tricresyl phosphate and 200 ml of ethyl acetate and a dispersion was prepared in the same manner as preparing Dispersion I. 1,150 g of the thus prepared dispersion was added to the above described emulsion and to which 25 ml of a 4% aqueous solution of Hardener (I) was added. The mixture was coated in a silver coated amount of 2.0 g/m².

Seventh Layer: Yellow Filter Layer

To 1 liter of an aqueous solution containing yellow colloidal silver and 50 g of gelatin, 200 g of Dispersion I and 25 ml of a 4% aqueous solution of Hardener (I) were added. The mixture was coated in a dry thickness of 1 micron.

Eighth Layer: Blue-Sensitive Emulsion Layer

To 1.0 kg of the same emulsion as was used in the third layer there were dissolved 100 g of Coupler (k), α-(4-methoxybenzoyl)-α-(1-benzyl-5-ethoxy-2,4-dioxo-3-hydantoinyl)-2-chloro-5-[α-(2,4-di-tert-amylphenoxy)butyramido]acetanilide in 100 ml of dibutyl phthalate and 200 ml of ethyl acetate, and 500 g of a dispersion which was prepared in the same manner as Dispersion I and 25 ml of a 4% aqueous solution of Hardener (I). The mixture was coated in a silver coated amount of 1.0 g/m².

Ninth Layer: Protective Layer

To 1 liter of an aqueous solution containing 100 g of gelatin, 25 ml of a 4% aqueous solution of Hardener (I) was added. The mixture was coated in a dry thickness of 1.0 micron.

The color negative light-sensitive material thus prepared was cut in a form suitable for use in a still camera, and photographed and processed according to the processing step described in Example 2.

The results obtained showed that the light-sensitive material using the coupler of the present invention provides a sufficiently high color density even when a reduced amount of silver halide is used in the green-sensitive layer and the red-sensitive layer and can be used to reduce the thickness of the emulsion layers resulting in further improving the sharpness of the images. Also, the color purity of the image was improved by using the novel colored coupler. Further, substantially no degradation in the graininess of the image was observed.

EXAMPLE 6

A silver iodobromide emulsion containing 4 mol% of iodide was coated in a dry thickness of 4.0 microns and a silver coated amount of 120 μg/cm² to prepare a film. The film was subjected to sensitometric stepwise exposure and then developed at 27° C for 4 minutes using the color developer solution set forth below and followed by washing, bleaching, washing, fixing, and washing in the same manner as described in Example 1 to provide a cyan color image.

| Color Developer Solution | | |
|---|---|---|
| Sodium sulfite | 5 | g |
| 4-Amino-3-methyl-N,N-diethylaniline hydrochloride | 0.6 | g |
| Sodium carbonate (monohydrate) | 15 | g |
| Potassium bromide | 0.5 | g |
| Potassium iodide (0.1% aq. soln.) | 5 | ml |
| Coupler (I), 2-Acetamido-6-chloro-4-dimethoxyphosphonyloxy-5-methylphenol | 1.2 | g |
| Sodium hydroxide | 2 | g |
| Water to make | 1,000 | ml |

The color image obtained had clear cyan color with an absorption maximum at 672 millimicrons.

EXAMPLE 7

A mixture of 53.5 g of the above described Coupler (14), 1-hydroxy-4-(n-dodecyloxy)ethoxyphosphonyloxy-(3',5'-dicarboxy)-2-naphthanilide, 55 ml of N,N-diethyllauryl amide and 75 ml of cyclohexanone was dissolved by heating to 70° C. The solution thus obtained was added to 600 ml of an aqueous solution containing 3.0 g of sodium p-dodecylbenzene sulfonate and 60 g of gelatin and stirred. The mixture was then passed five times through a heated colloid mill, whereby the coupler was finely dispersed together with the solvent.

All of the dispersion was mixed with 1.0 kg of a photographic emulsion containing 76.0 g of silver iodobromide containing 5.0 mol% of iodide, and 65 g of gelatin, and then, as a hardener, 25 ml of a 4% aqueous solution of 2-hydroxy-4,6-dichloro-s-triazine sodium salt was added thereto. The mixture was coated on a cellulose triacetate base in a dry thickness of 5.0 microns and on the layer, a gelatin layer, as a protective layer, was coated in a dry thickness of 1.0 micron to prepare a light-sensitive sheet material.

Also, onto a polyethylene terephthalate film base, the following layers were coated in this order to prepare an image-receiving material.

(1) A transparent layer comprising 300 mg/100 cm² of the half ester of a copolymer (monomer ratio: 1:1 molar) of vinyl methyl ether and maleic anhydride prepared by treating with butyl alcohol and 60 mg/100 cm² of 1,4-bis(2',3'-epoxypropoxy)butane was provided to prepare a neutralization layer.

(2) A neutralization rate-controlling layer comprising 45 mg/100 cm² of a copolymer (monomer ratio: 1:1 molar) of n-butylacrylate and β-hydroxyethylmethacrylate.

(3) An image receiving layer comprising 18 mg/100 cm² of cetyl-tri-n-butyl ammonium chloride, 40 mg/100 cm² of gelatin and 2 mg/100 cm² of tetramethylol urea.

(4) A covering layer of a thickness of about 0.5 micron provided by treating the surface with a 1% acetone solution of polyethyleneglycol monocetyl ether.

Further, a processing solution having the following composition and a rupturable container to be charged with the processing solution were prepared. The rupturable container was produced by folding a polyethylene-aluminum-cellophane-polyethylene laminate film and heat sealing the laminate film so as to form a cavity capable of containing the processing solution. The preparation of the processing solution and the charging of the processing solution into the container were carried out in a Freon gas atmosphere.

| Processing Solution | | |
|---|---|---|
| Ascorbic acid | 20 | mg |
| 4-Amino-3-methyl-N-ethyl-N-(β-hydroxyethyl)aniline sulfate (monohydrate) | 2.8 | g |
| 6-Nitrobenzimidazole nitrate | 15 | mg |
| Sodium hydroxide | 4 | g |
| Carboxymethyl cellulose sodium salt | 3.5 | g |
| Titanium dioxide | 45 | g |
| Water | 100 | ml |

The above described light-sensitive material and image receiving element were cut into size suitable for testing and they were arranged in such a manner that the coated layers faced each other. The container charged with the processing solution was attached to one edge between the two layers.

The film unit thus prepared was exposed to light and passed through a pair of rollers under pressure whereby the container was ruptured and the contents spread uniformly between the layers in a thickness of 120 microns.

After three minutes, a clear cyan negative image was formed on the image receiving material. The reflected optical density to red light was measured and the maximum density found to be 1.6 and the minimum density found to be 0.2.

EXAMPLE 8

10 g of the above described Coupler (21), 1-(2,4,6-trichlorophenyl)-3-{3-[(2,3-di-tert-amylphenoxy)acetamido]-benzamido}-4-diethoxyphosphonyloxy-5-pyrazolone, was added to 10 ml of tricresyl phosphate and 20 ml of ethyl acetate and dissolved by heating at 50° C. The solution was added to 100 ml of an aqueous solution containing 10 g of gelatin and 0.5 g of sodium p-dodecylbenzene sulfonate and subjected to vigorous mechanical stirring. The coupler was finely dispersed together with the solvent.

92.5 g of the coupler dispersion was added to 100 g of a silver chlorobromide emulsion containing 50 mol% of bromide, $3.0 \times 10^{-2}$ mole of silver and 8 g of gelatin, to which 14 ml of a 2% aqueous solution of 2-hydroxy-4,6-dichloro-s-triazine sodium salt was added as a hardener. The pH of the mixture was adjusted to 6.0 and then the mixture was coated on a cellulose triacetate film base in a silver coated amount of $5.0 \times 10^{-5}$ g/cm². This film was designated Sample F. The coated amount of the coupler in Sample F was $1.16 \times 10^{-7}$ mol/cm².

For comparison, using 10 g of Coupler (l), 1-(2,4,6-trichlorophenyl)-3-{3-[(2,4-di-tert-amylphenoxy)acetamido]-benzamido}-5-pyrazolone in place of Coupler (21), a fine coupler dispersion was prepared in an identical manner.

76 g of the coupler dispersion was added to 200 g of the same emulsion as described above and using the same procedure as described above except adding 21 ml of the same hardener solution and coating in a silver coated amount of $1.0 \times 10^{-4}$ g/cm² another film was prepared. This film was designated Sample G. The coated amount of the coupler in Sample G was $1.21 \times 10^{-7}$ mol/cm².

These samples were subjected to sensitometric stepwise exposure followed by processing in the same manner as described in Example 1.

After the processing, the optical density to green light of Samples F and G was measured to obtain the results shown in Table 4.

TABLE 4

| Film Sample | Coupler | Coupler Coated Amount (mol/m²) | Fog | Sensitivity* (relative value) | Gamma | Maximum Density |
|---|---|---|---|---|---|---|
| F | (21) | $1.16 \times 10^{-7}$ | 0.09 | 100 | 2.31 | 2.77 |
| G | (l) | $1.21 \times 10^{-7}$ | 0.05 | 94 | 1.68 | 2.32 |

*Amount of exposure required to give a density of fog + 0.10.

These results show that the coupler in which the active position is substituted with a phosphonyloxy group used in the present invention gives higher sensitivity, gradation and color density, in comparison with those of a coupler in which the active position is unsubstituted, such as Coupler (l).

Further, the coupler substituted with a phosphonyloxy group gave a high maximum density in spite of the fact that the coated amount of coupler per unit area was the same as that of the active position unsubstituted couplers. This means that the coupler of the present invention has a high conversion rate to dye, and, thus, it is possible to reduce the coated amount of silver to one half and also to reduce the coated amount of coupler to obtain a sufficient color density.

While the invention has been described in detail and with reference to specific embodiments thereof, it will be apparent to one skilled in the art that various changes and modifications can be made therein without departing from the spirit and scope thereof.

What is claimed is:

1. A method for forming color images which comprises developing a silver halide photographic light-sensitive material in the presence of a photographic color coupler in which a hydrogen atom at the coupling position capable of coupling with an oxidation product of an aromatic primary amine developing agent is substituted with the group represented by the following general formula:

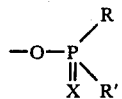

wherein R and R', which may be the same or different, each represents an alkyl group, an alkenyl group, an aryl group, an alkoxy group, an alkylthio group, an aryloxy group, a hydroxy group or an amino group; R and R' can combine each other to form a ring, and X represents an oxygen atom or a sulfur atom.

2. The method as claimed in claim 1, wherein said coupler is represented by the following general formula (I):

$$A-O-P\underset{X}{\overset{R}{\diagdown}}R'$$  (I)

wherein A represents an image forming coupler residue containing a naphthol nucleus, a phenol nucleus, a 5-pyrazolone nucleus, a pyrazolobenzimidazole nucleus, a malondiamide nucleus or a cyanoacetanilide nucleus; the group

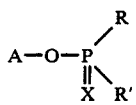

is bonded to the coupling position of the coupler residue; and R, R' and X each has the same meaning as defined in claim 1.

3. The method as claimed in claim 1, wherein said coupler is represented by the following general formula (II):

$$R_1-A_1-O-P\underset{X}{\overset{R}{\diagdown}}R'$$  (II)

wherein $A_1$ represents a cyan image forming coupler residue containing a phenol nucleus or an α-naphthol nucleus, a magenta image forming coupler residue containing a 5-pyrazolone nucleus or a pyrazolobenzimidazole nucleus or a yellow image forming coupler residue containing a pivaloylacetanilide nucleus or a benzoylacetanilide nucleus; R, R' and X each has the same meaning as defined in claim 1; and $R_1$ represents a hydrogen atom, a halogen atom, a nitro group, a cyano group, a hydroxy group, a sulfo group, a carboxy group, an alkyl group, an alkoxy group, an aryloxy group, an acylamino group, a carbamoyl group, an oxycarbonyl group or a sulfamoyl group.

4. The method as claimed in claim 3, wherein said coupler is represented by general formula (XII):

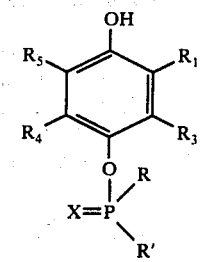

wherein R, R', R and X each has the same meaning as R, R', $R_1$ and X in general formula (II), $R_3$, $R_4$ and $R_5$ each represents a hydrogen atom, a halogen atom, an alkyl group, an aryl group, an alkoxy group, an alkylthio group, a heterocyclic group, an amino group, a carbonamido group, a sulfonamido group, a sulfamoyl group or a carbamoyl group.

5. The method as claimed in claim 3, wherein said coupler is represented by general formula (XIII):

(XIII)

wherein R, R' and X each has the same meaning as R, R' and X in general formula (II), $R_2$ represents a hydrogen atom, an alkyl group having 30 or less carbon atoms, or a carbamoyl group represented by general formulae (VII) and (VIII) described below, $R_3$, $R_4$, $R_5$, $R_6$ and $R_7$ each represents a hydrogen atom, a halogen atom, an alkyl group, an aryl group, an alkoxy group, an alkylthio group, a heterocyclic group, an amino group, a carbonamido group, a sulfonamido group, a sulfamoyl group or a carbamoyl group, and W represents the non-metallic atomic group necessary to form a 5-membered or 6-membered ring;

$$-CONHZ$$  (VII)

$$-CON\underset{Y'}{\overset{Y}{\diagdown}}$$  (VIII)

wherein Z represents a straight or branched chain alkyl group having 1 to 32 carbon atoms, a cycloalkyl group or an aryl group, and wherein Y and Y' can have the same meaning as Z, or can be represented by the formulae —OZ, —NH—Z or $$-N\underset{Z}{\overset{Z}{\diagdown}}$$

6. The method as claimed in claim 3, wherein said coupler is represented by general formula (XIV):

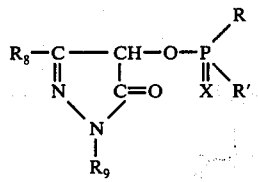

(XIV)

wherein R, R' and X each has the same meaning as R, R' and X in general formula (II), $R_8$ represents an alkyl group, an alkoxy group, a ureido group, or a substituted amino group, and $R_9$ represents an alkyl group.

7. The method as claimed in claim 3, wherein said coupler is represented by general formula (XV):

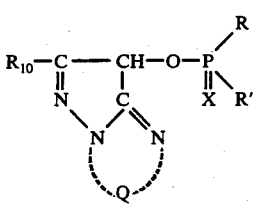

(XV)

wherein R, R' and X each has the same meaning as R, R' and X in general formula (II), $R_{10}$ represents an alkyl group, an alkoxy group, a ureido group, or a substituted amino group, and Q represents the atomic group necessary to form a heterocyclic ring.

8. The method as claimed in claim 3, wherein said coupler is represented by general formula (XVI):

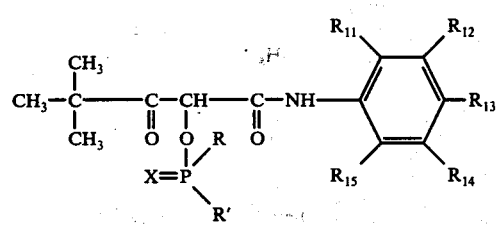

(XVI)

wherein R, R' and X each has the same meaning as R, R' and X in general formula (II), $R_{11}$ represents a hydrogen atom, a halogen atom, a nitro group, a cyano group, a hydroxy group, a sulfo group, a carboxy group, an alkyl group having 1 to 20 carbon atoms, an alkoxy group having 1 to 20 carbon atoms, an aryloxy group, an acylamino group as represented by general formulae (III) to (VI) below, a carbamoyl group as represented by general formulae (VII) or (VIII) below, an oxycarbonyl group as represented by general formula (IX) below or a sulfamoyl group as represented by general formulae (X) or (XI) below; and $R_{12}$, $R_{13}$, $R_{14}$ and $R_{15}$ each represents a group as defined for $R_{11}$;

| | |
|---|---|
| —NH—CO—Z | (III) |
| —NH—SO$_2$Z | (IV) |
| 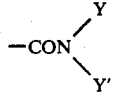 | (V) |
| —NHCONHZ | (VI) |
| —CONHZ | (VII) |

-continued

| | |
|---|---|
|  | (VIII) |
| —COOZ | (IX) |
| —SO$_2$—NH—Z | (X) |
| —SO$_2$N$\diagdown^Y_{Y'}$ | (XI) | wherein Z represents a straight or branched chain alkyl group having 1 to 32 carbon atoms, a cycloalkyl group or an aryl group; and Y and Y' can each have the same meaning as Z and in addition can be —OZ, —NH—Z or $$-N\diagdown^Z_Z.$$

9. The method as claimed in claim 3, wherein said coupler is represented by general formula (XVII):

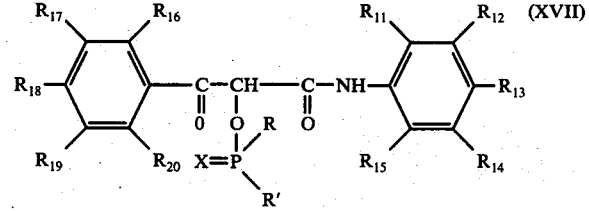

(XVII)

wherein R, R' and X each has the same meaning as R, R' and X in general formula (II), $R_{11}$ represents a hydrogen atom, a halogen atom, a nitro group, a cyano group, a hydroxy group, a sulfo group, a carboxy group, an alkyl group having 1 to 20 carbon atoms, an alkoxy group having 1 to 20 carbon atoms, an aryloxy group, an acylamino group as represented by general formulae (III) to (VI) below, a carbamoyl group as represented by general formulae (VII) or (VIII) below, an oxycarbonyl group as represented by general formula (IX) below or a sulfamoyl group as represented by general formulae (X) or (XI) below; and $R_{12}$, $R_{13}$, $R_{14}$ and $R_{15}$ each represents a group as defined for $R_{11}$;

| | |
|---|---|
| —NH—CO—Z | (III) |
| —NH—SO$_2$Z | (IV) |
| —NH—P$\diagdown^Y_{Y'}$ (with =O) | (V) |
| —NHCONHZ | (VI) |
| —CONHZ | (VII) |
| —CON$\diagdown^Y_{Y'}$ | (VIII) |
| —COOZ | (IX) |
| —SO$_2$—NH—Z | (X) |

-continued

wherein Z represents a straight or branched chain alkyl group having 1 to 32 carbon atoms, a cyaloalkyl group or an aryl group; and Y and Y' can each have the same meaning as Z and in addition can be —OZ, —NH—Z or

and $R_{16}$, $R_{17}$, $R_{18}$, $R_{19}$ $R_{20}$ each represents a group as defined for $R_{11}$.

10. The method as claimed in claim 3, wherein said coupler is selected from the cyan dye forming two-equivalent couplers represented by the following formulae:

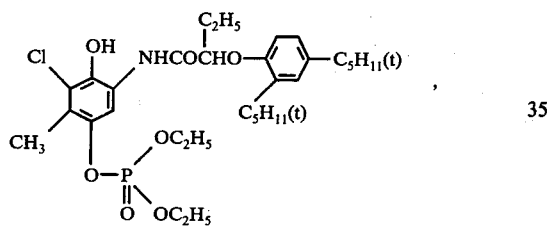

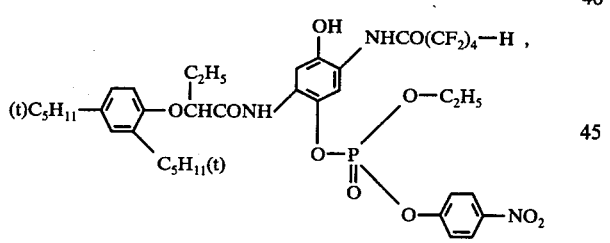

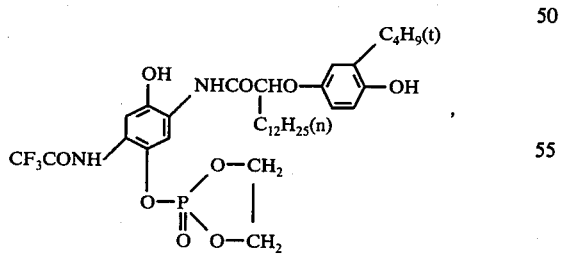

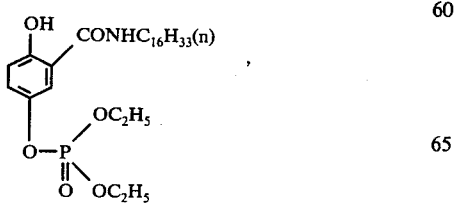

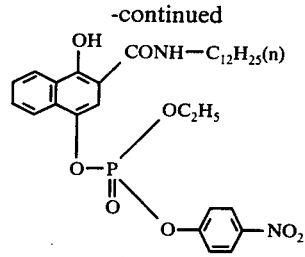

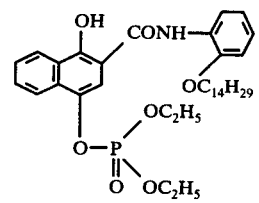

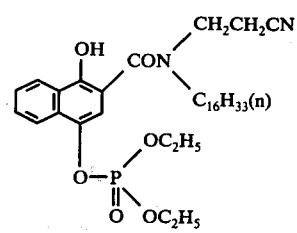

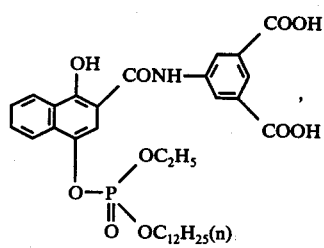

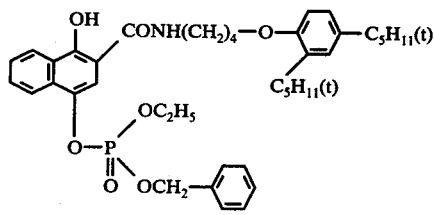

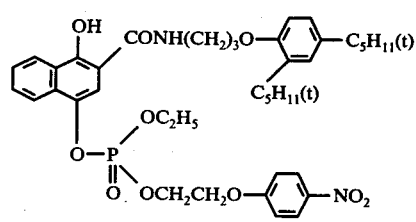

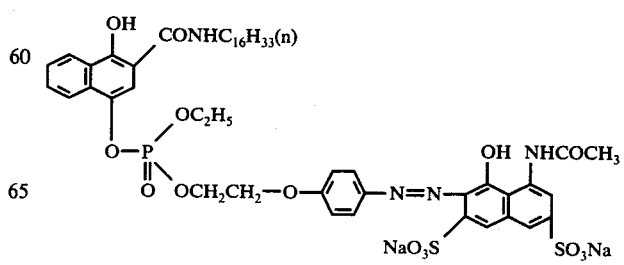

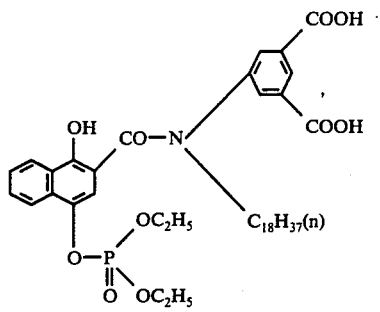
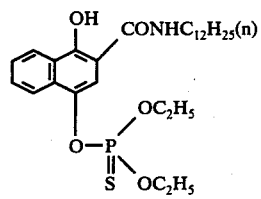
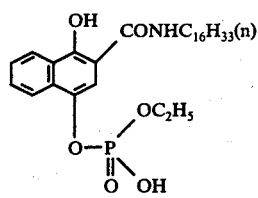
and
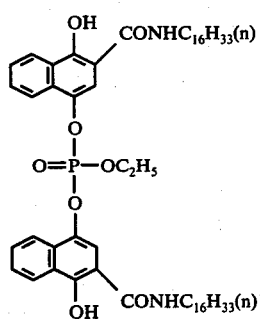
11. The method as claimed in claim 3, wherein said coupler is selected from the magenta dye image forming two-equivalent couplers as represented by the formulae:
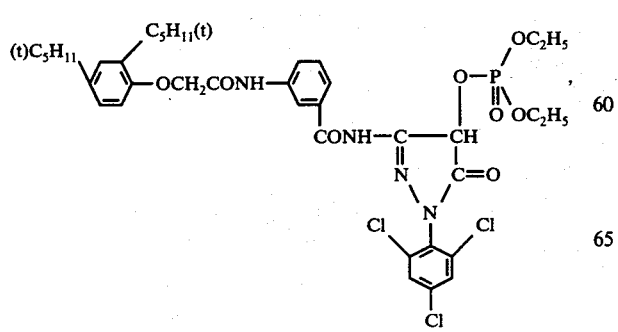
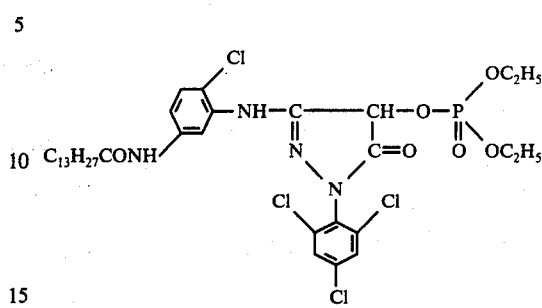
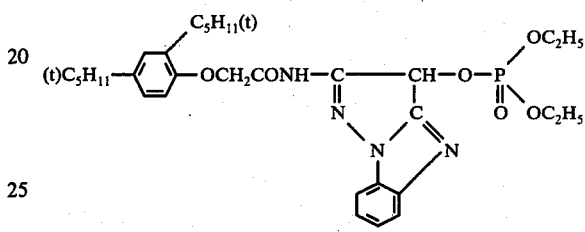
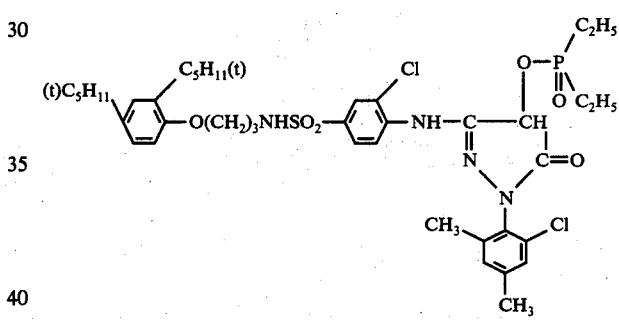
and
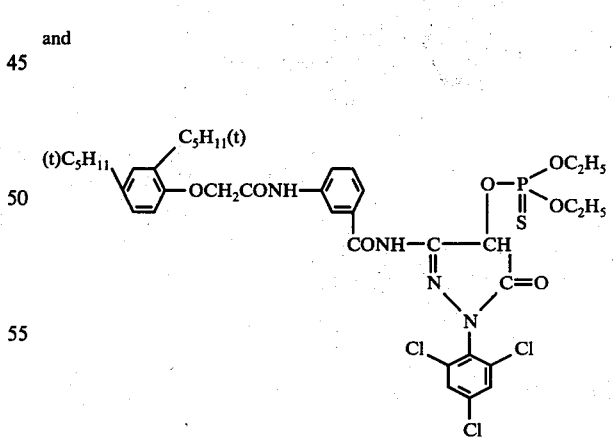
12. The method as claimed in claim 3, wherein said coupler is selected from the yellow dye image forming two-equivalent couplers as represented by the formulae:

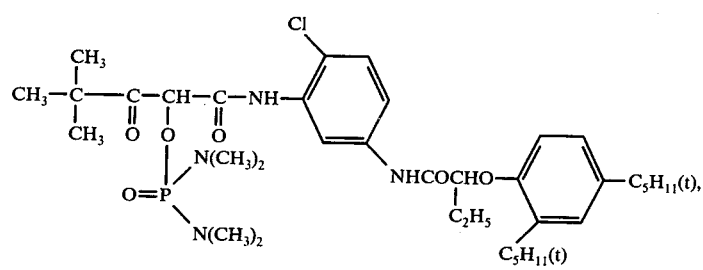
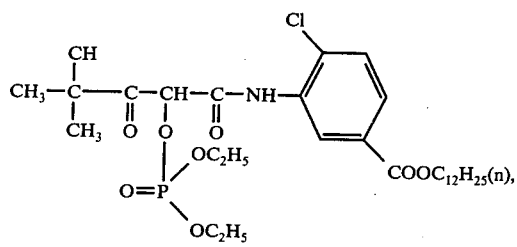
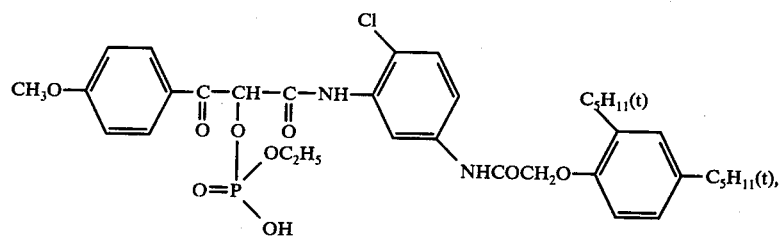
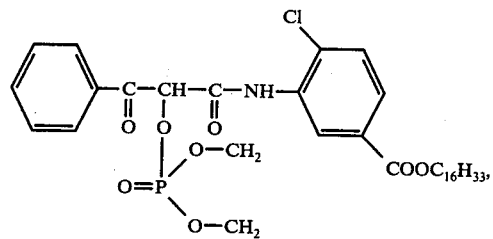
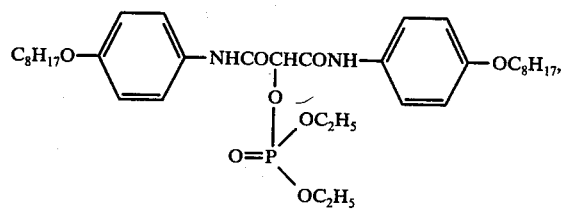
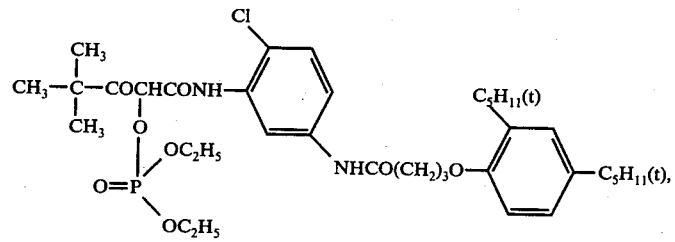
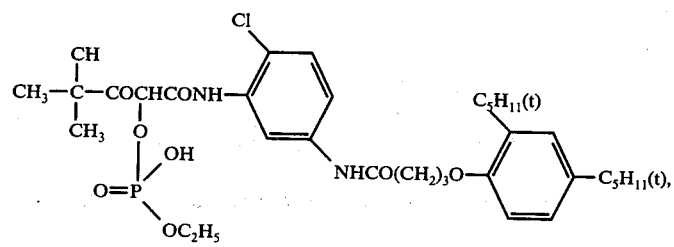

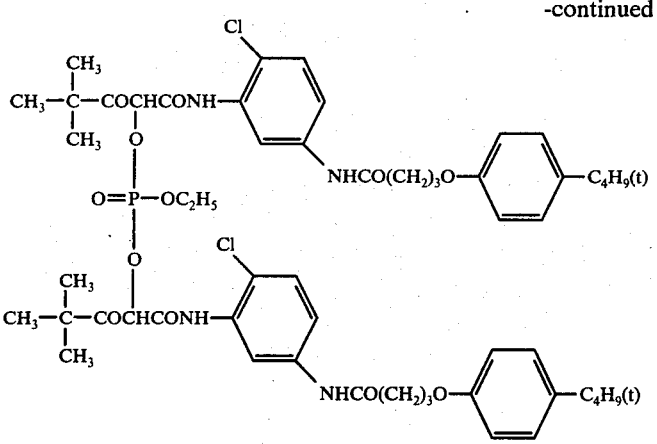

and

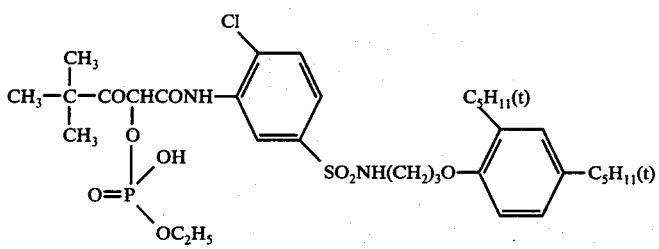

13. A photographic silver halide emulsion containing a photographic color coupler in which a hydrogen atom at the coupling position capable of coupling with an oxidation product of an aromatic primary amine developing agent is substituted with the group represented by the following general formula:

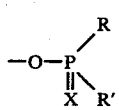

wherein R and R', which may be the same or different, each represents an alkyl group, an alkenyl group, an aryl group, an alkoxy group, an alkylthio group, an aryloxy group, a hydroxy group or an amino group; R and R' can combine each other to form a ring, and X represents an oxygen atom or a sulfur atom.

14. A photographic light-sensitive material comprising a support having thereon the photographic silver halide emulsion as claimed in claim 13.

15. A photographic light-sensitive material comprising a support having thereon a blue-sensitive silver halide emulsion layer, a green-sensitive silver halide emulsion layer and a red-sensitive silver halide emulsion layer, and at least one of the emulsion layers contains a photographic color coupler in which a hydrogen atom at the coupling position capable of coupling with an oxidation product of an aromatic primary amine developing agent is substituted with the group represented by the following general formula:

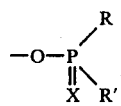

wherein R and R', which may be the same or different, each represents an alkyl group, an alkenyl group, an aryl group, an alkoxy group, an alkylthio group, an aryloxy group, a hydroxy group or an amino group; R and R' can combine each other to form a ring, and X represents an oxygen atom or a sulfur atom.

16. A method of forming color images which comprises developing the photographic light-sensitive material as claimed in claim 14 with an aqueous alkaline solution containing a primary aromatic amine developing agent.

17. The method as claimed in claim 16, wherein said coupler is represented by the following general formula (I):

wherein A represents an image forming coupler residue containing a naphthol nucleus, a phenol nucleus, a 5-pyrazolone nucleus, a pyrazolobenzimidazole nucleus, a malondiamide nucleus or a cyanoacetanilide nucleus; the group

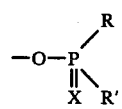

is bonded to the coupling position of the coupler residue; and R, R' and X each has the same meaning as defined in claim 1.

18. The method as claimed in claim 16, wherein said coupler is represented by the following general formula (II):

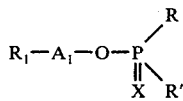 (II)

wherein $A_1$ represents a cyan image forming coupler residue containing a phenol nucleus or an α-naphthol nucleus, a magenta image forming coupler residue containing a 5-pyrazolone nucleus or a pyrazolobenzimidazole nucleus or a yellow image forming coupler residue containing a pivaloylacetanilide nucleus or a benzoylacetanilide nucleus; R, R' and X each has the same meaning as defined in claim 1; and $R_1$ represents a hydrogen atom, a halogen atom, a nitro group, a cyano group, a hydroxy group, a sulfo group, a carboxy group, an alkyl group, an alkoxy group, an aryloxy group, an acylamino group, a carbamoyl group, an oxycarbonyl group or a sulfamoyl group.

19. The method as claimed in claim 18, wherein said coupler is represented by general formula (XII):

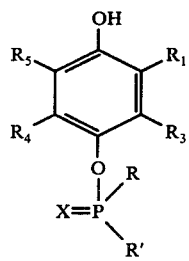 (XII)

wherein R, R', R and X each has the same meaning as R, R', $R_1$ and X in general formula (II), $R_3$, $R_4$ and $R_5$ each represents a hydrogen atom, a halogen atom, an alkyl group, an aryl group, an alkoxy group, an alkylthio group, a heterocyclic group, an amino group, a carbonamido group, a sulfonamido group, a sulfamoyl group or a carbomoyl group.

20. The method as claimed in claim 18, wherein said coupler is represented by general formula (XIII):

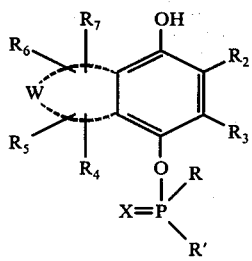 (XIII)

wherein R, R' and X each has the same meaning as R, R' and X in general formula (II), $R_2$ represents a hydrogen atom, an alkyl group having 30 or less carbon atoms, or a carbamoyl group represented by general formulae (VII) and (VIII) described below, $R_3$, $R_4$, $R_5$, and $R_7$ each represents a hydrogen atom, a halogen atom, an alkyl group, an aryl group, an alkoxy group, an alkylthio group, a heterocyclic group, an amino group, a carbonamido group, a sulfonamido group, a sulfamoyl group or a carbamoyl group, and W represents the non-metallic atomic group necessary to form a 5-membered or 6-membered ring;

—CONHZ (VII)

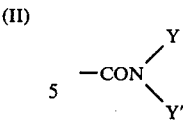 (VIII)

wherein Z represents a straight or branched chain alkyl group having 1 to 32 carbon atoms, a cycloalkyl group or an aryl group, and wherein Y and Y' can have the same meaning as Z, or can be represented by the formulae —OZ, —NH-Z or

21. The method as claimed in claim 18, wherein said coupler is represented by general formula (XIV):

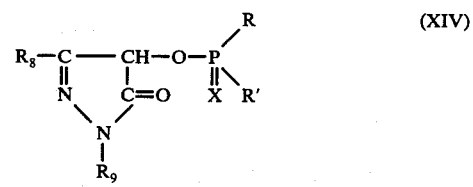 (XIV)

wherein R, R' and X each has the same meaning as R, R' and X in general formula (II), $R_8$ represents an alkyl group, an alkoxy group, a ureido group, or a substituted amino group, and $R_9$ represents an alkyl group.

22. The method as claimed in claim 18, wherein said coupler is represented by general formula (XV):

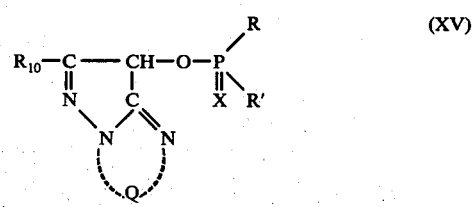 (XV)

wherein R, R' and X each has the same meaning as R, R' and X in general formula (II), $R_{10}$ represents an alkyl group, an alkoxy group, a ureido group, or a substituted amino group, and Q represents the atomic group necessary to form a heterocyclic ring.

23. The method as claimed in claim 18, wherein said coupler is represented by general formula (XVI):

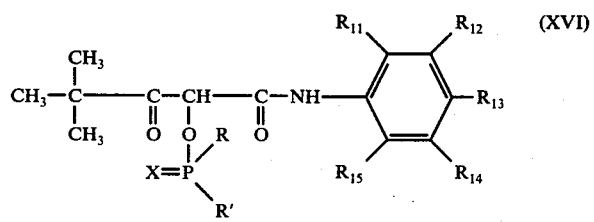 (XVI)

wherein R, R' and X each has the same meaning as R, R' and X in general formula (II), $R_{11}$ represents a hydrogen atom, a halogen atom, a nitro group, a cyano group, a hydroxy group, a sulfo group, a carboxy group, an alkyl group having 1 to 20 carbon atoms, an alkoxy group having 1 to 20 carbon atoms, an aryloxy group, an acylamino group as represented by general formulae (III) to (VI) below, a carbamoyl group as represented by general formulae (VII) or (VIII) below, an oxycarbonyl group as represented by general formula (IX) below or a sulfamoyl group as represented by general formulae (X) or (XI) below; and $R_{12}$, $R_{13}$, $R_{14}$ and $R_{15}$ each represents a group as defined for $R_{11}$;

$$-NH-CO-Z \quad (III)$$
$$-NH-SO_2Z \quad (IV)$$
$$-NH-\underset{\underset{O}{\|}}{P}\underset{Y'}{\overset{Y}{\diagup}} \quad (V)$$
$$-NHCONHZ \quad (VI)$$
$$-CONHZ \quad (VII)$$
$$-CON\underset{Y'}{\overset{Y}{\diagup}} \quad (VIII)$$
$$-COOZ \quad (IX)$$
$$-SO_2-NH-Z \quad (X)$$
$$-SO_2N\underset{Y'}{\overset{Y}{\diagup}} \quad (XI)$$

wherein Z represents a straight or branched chain alkyl group having 1 to 32 carbon atoms, a cycloalkyl group or an aryl group; and Y and Y' can each have the same meaning as Z and in addition can be —OZ, —NH—Z or

24. The method as claimed in claim 18, wherein said coupler is represented by general formula (XVII):

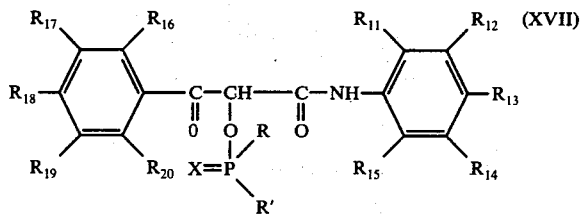

wherein R, R' and X each has the same meaning as R, R' and X in general formula (II), $R_{11}$ represents a hydrogen atom, a halogen atom, a nitro group, a cyano group, a hydroxy group, a sulfo group, a carboxy group, an alkyl group having 1 to 20 carbon atoms, an alkoxy group having 1 to 20 carbon atoms, an aryloxy group, an acylamino group as represented by general formulae (III) to (VI) below, a carbamoyl group as represented by general formulae (VII) or (VIII) below, an oxycarbonyl group as represented by general formula (IX) below or a sulfamoyl group as represented by general formulae (X) or (XI) below; and $R_{12}$, $R_{13}$, $R_{14}$ and $R_{15}$ each represents a group as defined for $R_{11}$;

$$-NH-CO-Z \quad (III)$$
$$-NH-SO_2Z \quad (IV)$$
$$-NH-\underset{\underset{O}{\|}}{P}\underset{Y'}{\overset{Y}{\diagup}} \quad (V)$$
$$-NHCONHZ \quad (VI)$$
$$-CONHZ \quad (VII)$$
$$-CON\underset{Y'}{\overset{Y}{\diagup}} \quad (VIII)$$
$$-COOZ \quad (IX)$$
$$-SO_2-NH-Z \quad (X)$$
$$-SO_2N\underset{Y'}{\overset{Y}{\diagup}} \quad (XI)$$

wherein Z represents a straight or branched chain alkyl group having 1 to 32 carbon atoms, a cyoloalkyl group or an aryl group; and Y and Y' can each have the same meaning as Z and in addition can be —OZ, —NH—Z or

and $R_{16}$, $R_{17}$, $R_{18}$, $R_{19}$ and $R_{20}$ each represents a group as defined for $R_{11}$.

25. The method as claimed in claim 18, wherein said coupler is selected from the cyan dye forming two-equivalent couplers represented by the following formulae:

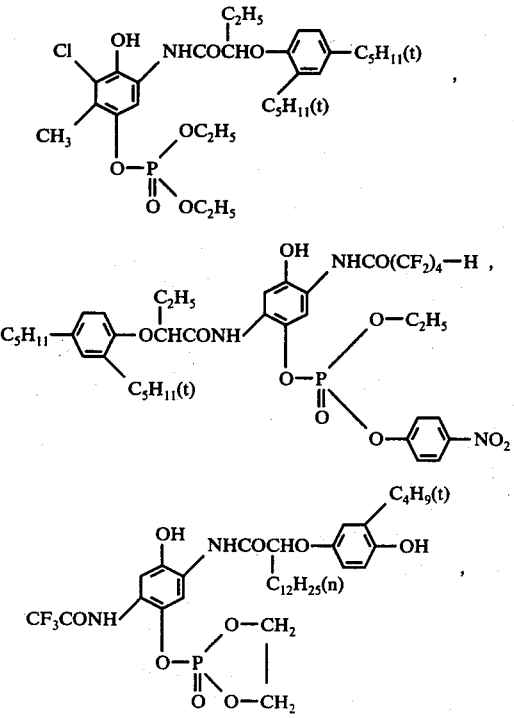

-continued
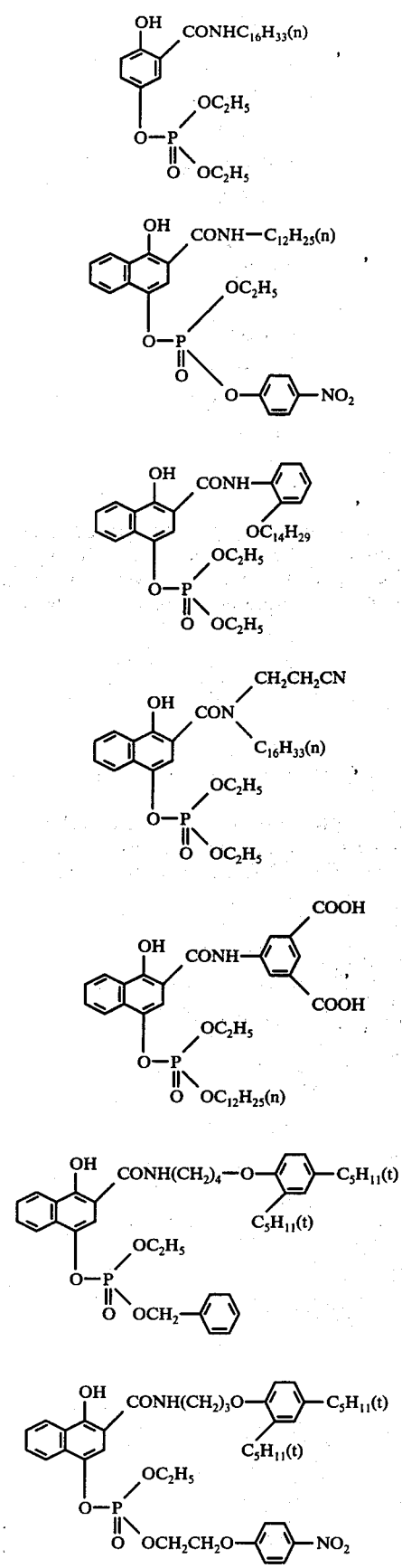
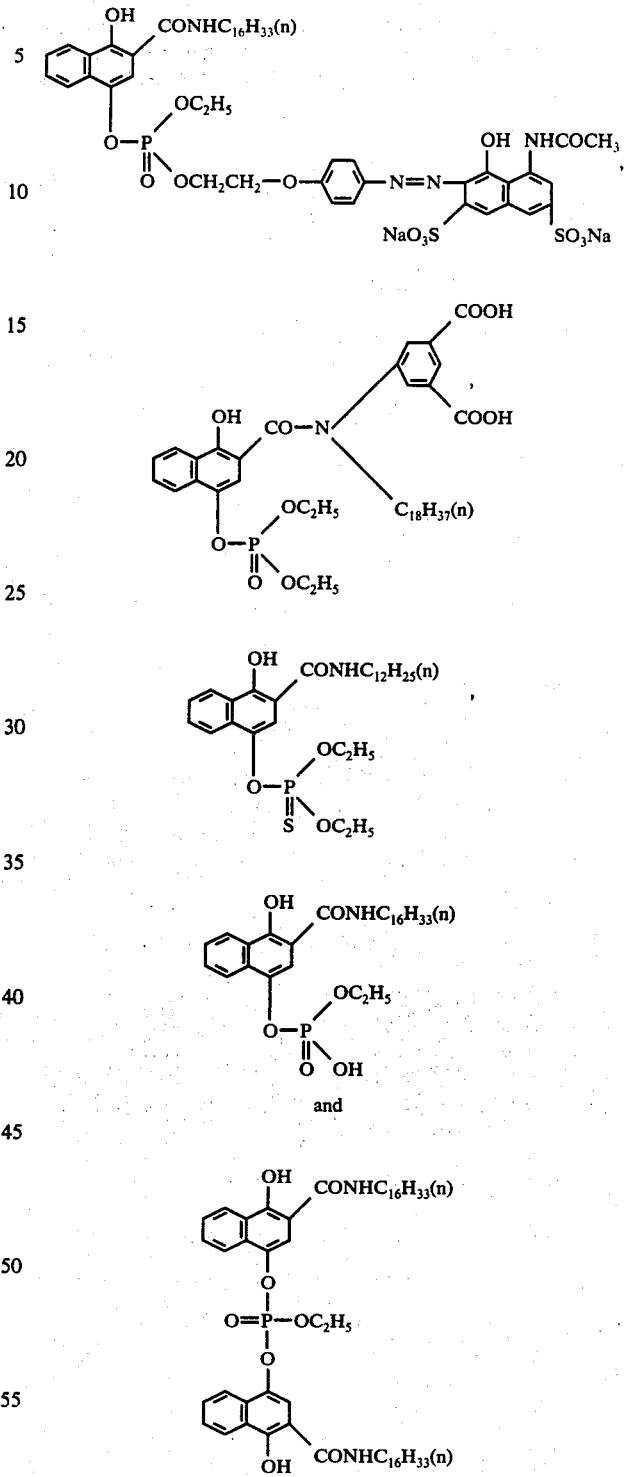
26. The method as claimed in claim 18, wherein said coupler is selected from the magenta dye image forming two-equivalent couplers as represented by the formulae:

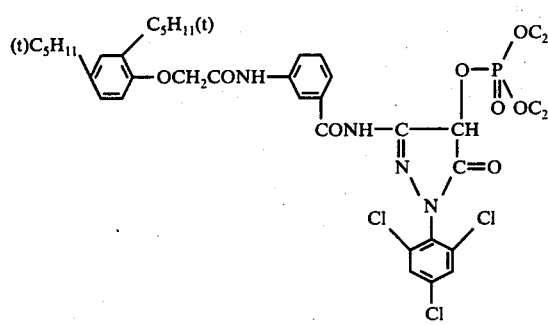
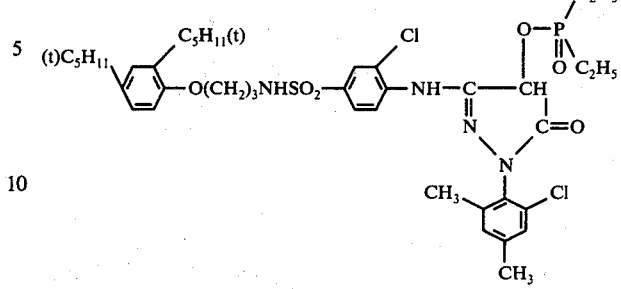
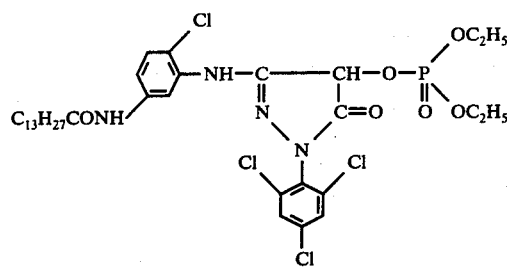
and
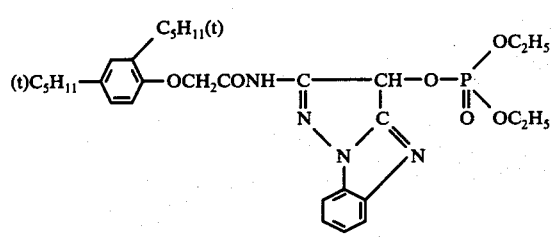
27. The method as claimed in claim 18, wherein said coupler is selected from the yellow dye image forming two-equivalent couplers as represented by the formulae:
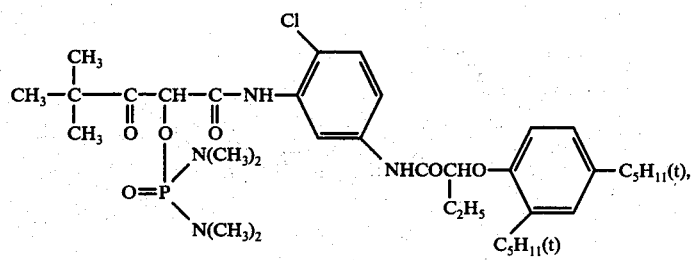
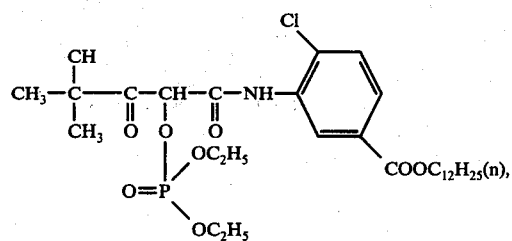
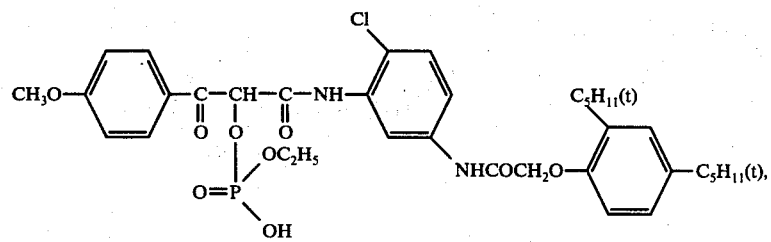

-continued
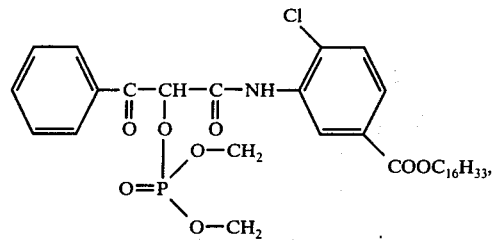
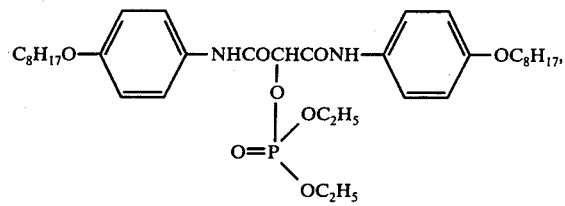
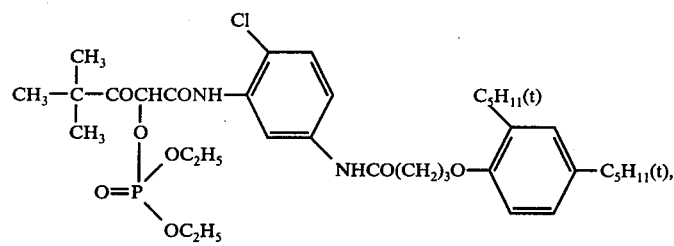
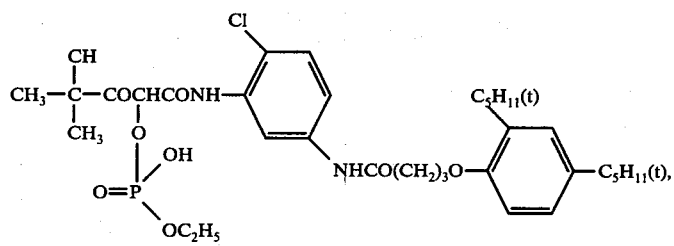
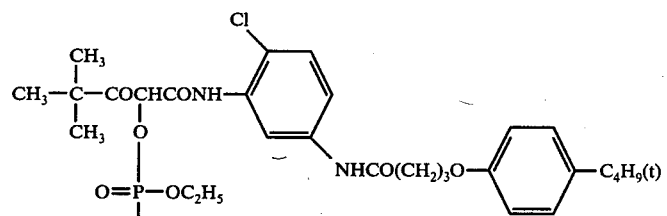
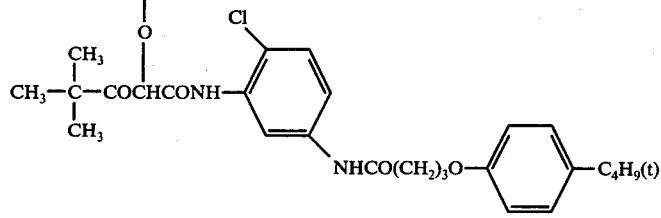
and
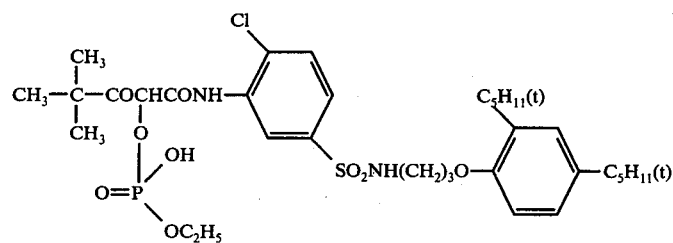
* * * * *